US009169322B2

(12) United States Patent
Bogen et al.

(10) Patent No.: US 9,169,322 B2
(45) Date of Patent: Oct. 27, 2015

(54) MODIFIED ANTIBODY

(75) Inventors: Bjarne Bogen, Snaroya (NO); Agnete Brunsvik Fredriksen, Raelingen (NO); Inger Sandlie, Oslo (NO)

(73) Assignee: Vaccibody AS, Oslo (NO)

( * ) Notice: Subject to any disclaimer, the term of this patent is extended or adjusted under 35 U.S.C. 154(b) by 488 days.

(21) Appl. No.: 13/353,548

(22) Filed: Jan. 19, 2012

(65) Prior Publication Data

US 2012/0171242 A1    Jul. 5, 2012

Related U.S. Application Data

(62) Division of application No. PCT/NO2004/000051, filed on Feb. 25, 2004, and a division of application No. 10/786,907, filed on Feb. 25, 2004.

(60) Provisional application No. 60/450,134, filed on Feb. 25, 2003.

(51) Int. Cl.
*C07K 16/28*    (2006.01)
*C07K 16/44*    (2006.01)
*A61K 39/00*    (2006.01)

(52) U.S. Cl.
CPC ............. *C07K 16/2833* (2013.01); *C07K 16/44* (2013.01); *A61K 2039/505* (2013.01); *A61K 2039/54* (2013.01); *C07K 2317/31* (2013.01); *C07K 2317/622* (2013.01)

(58) Field of Classification Search
CPC .................... C07K 16/2833; C07K 2317/622; C07K 2317/31; A61K 2039/54; A61K 2039/505

USPC .......... 424/198.1, 184.1, 204.1, 208.1, 234.1, 424/248.1
See application file for complete search history.

(56) References Cited

U.S. PATENT DOCUMENTS

2004/0253238 A1* 12/2004 Bogen et al. ............... 424/144.1
2013/0336971 A9* 12/2013 Ruffini et al. .............. 424/134.1

OTHER PUBLICATIONS

Rochlitz C. F. (Swiss Medicine Weekly, 131:4-9, 2001).*
Verma (Nature, vol. 389, pp. 239-242, 1997).*
Glick (Gen. Engineer. News 28(7) pp. 6 and 9 (Apr. 1, 2008).*
Haupt et al. (Exp Biol Med 227(4):227-237 (2002)).*
Bronte (Curr. Gene Therapy 1:53-100 (2001)).*
Lewis, A.D., et al., "Generation of Neutralizing Activity against Human Immunodeficiency Virus Type 1 in Serum by Antibody Gene Transfer", *J. Virol.*, 76 (17), pp. 8769-8775, 2002.
Noel, D., et al., "High in vivo production of a model monoclonal antibody on adenoviral gene transfer", *Hum. Gene Ter.*, 13(12), pp. 1483-1493, 2002 (abstract only).

* cited by examiner

*Primary Examiner* — Lynn Bristol
(74) *Attorney, Agent, or Firm* — Harness, Dickey & Pierce, PLC

(57) ABSTRACT

Recombinant antibody-based molecules that trigger both T-cell and B-cell immune responses are disclosed. The recombinant molecules are comprised by at least one targeting unit and at least one antigenic unit connected through a dimerization motif. Also disclosed are nucleic acid molecules encoding the recombinant antibody-based molecule and methods of treating multiple myeloma or lymphoma in a patient using the recombinant antibody-based molecules or the nucleic acid molecules.

29 Claims, 25 Drawing Sheets

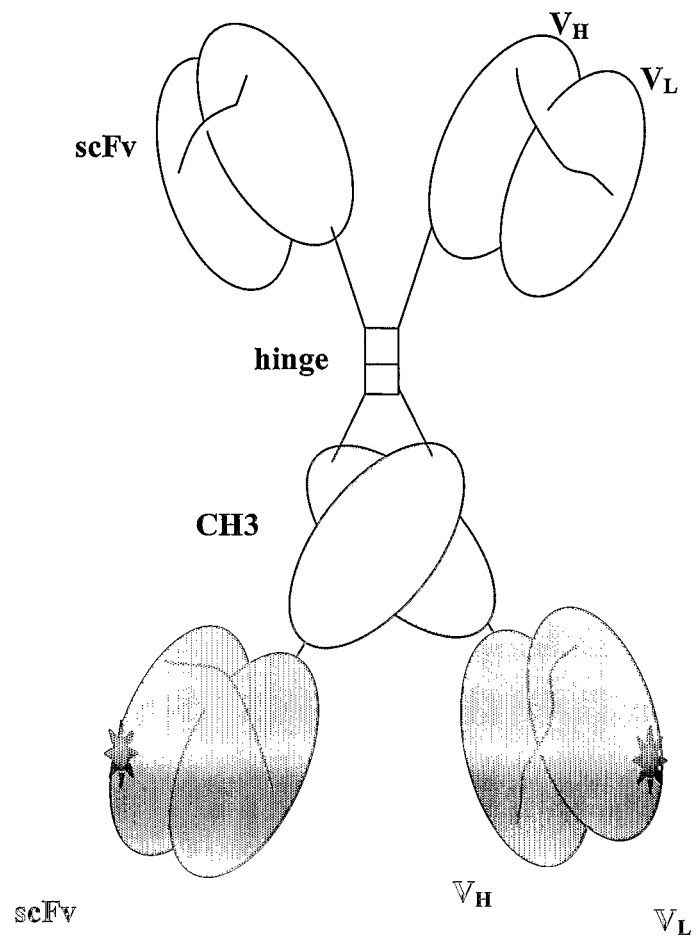
Fig 1 The structure of the Vaccibody.

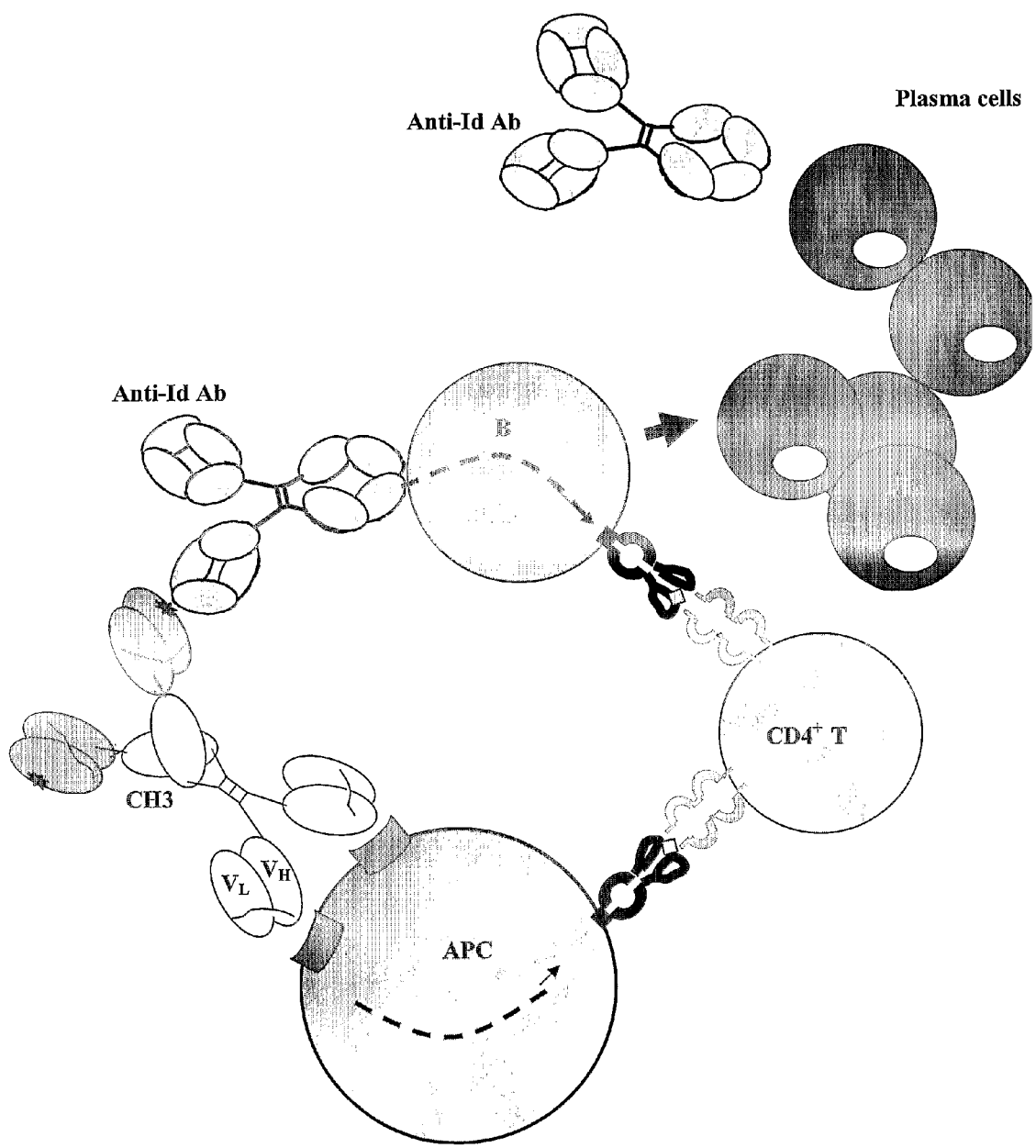
Fig 2 Principle.

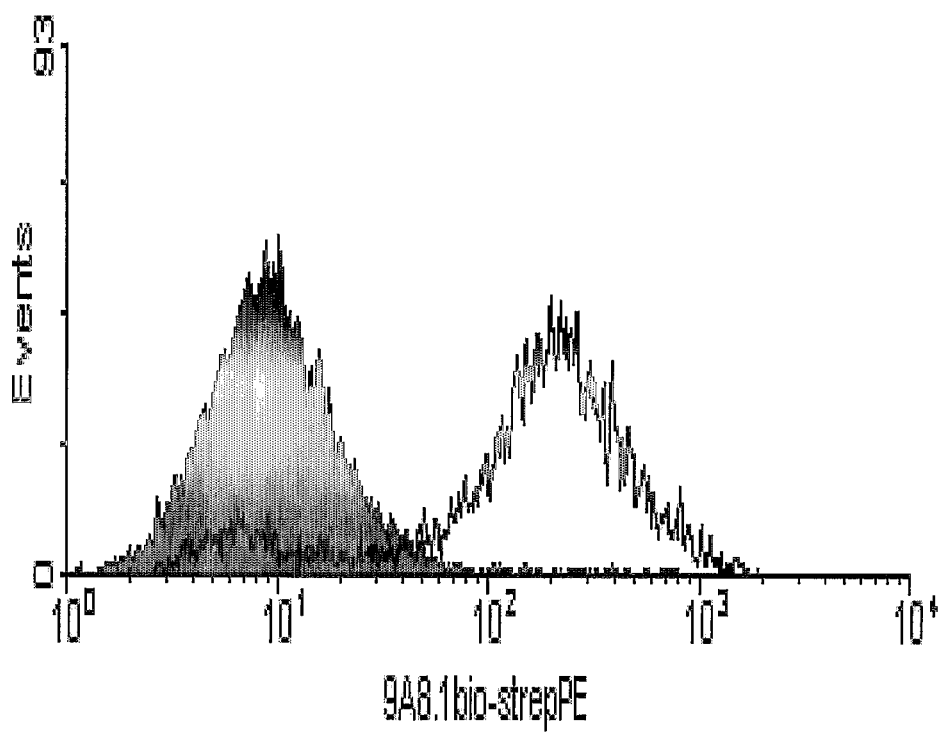
Fig 3 Flow cytometry of splenocytes

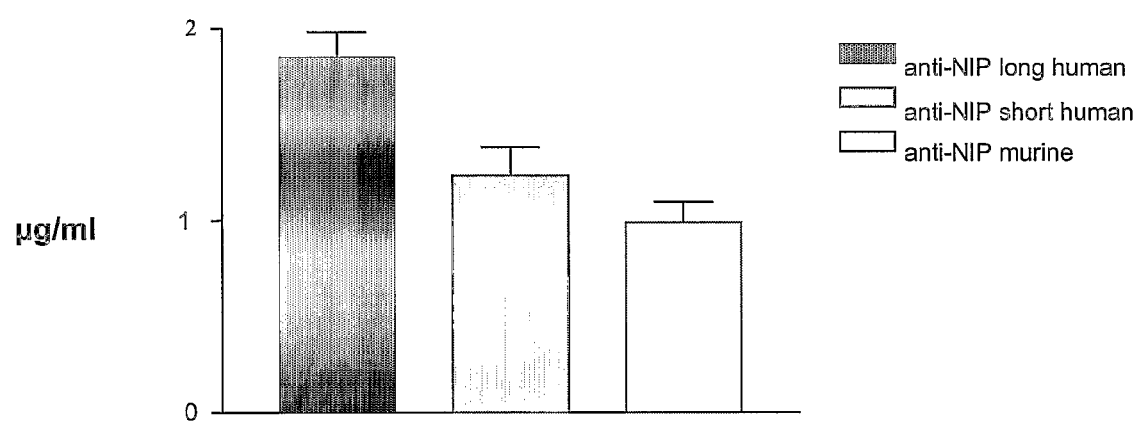
Fig 4 The NIP-specific control Vaccibodies exhibits binding to the hapten NIP.

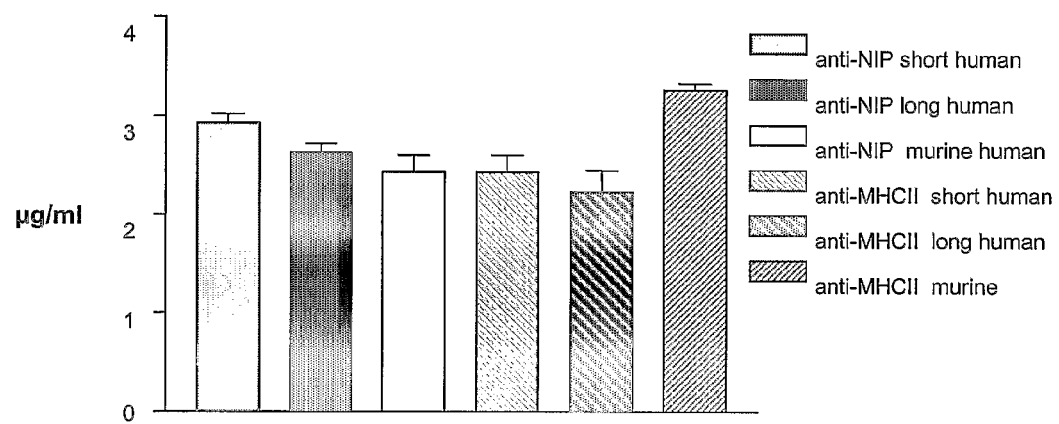
Fig 5 The Vaccibodies exhibit binding to DNP, hence the antigenic scFv is correctly folded.

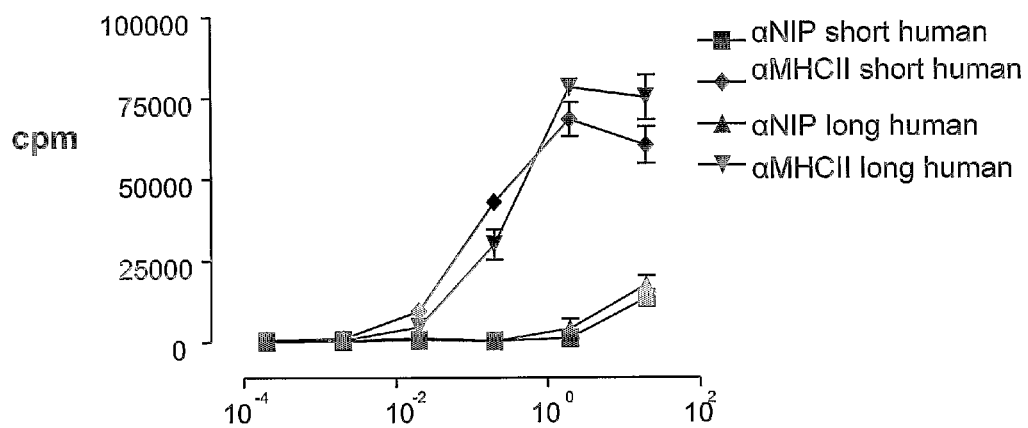
Fig 6 APC pulsed with titrated amounts of MHC class II specific Vaccibodies

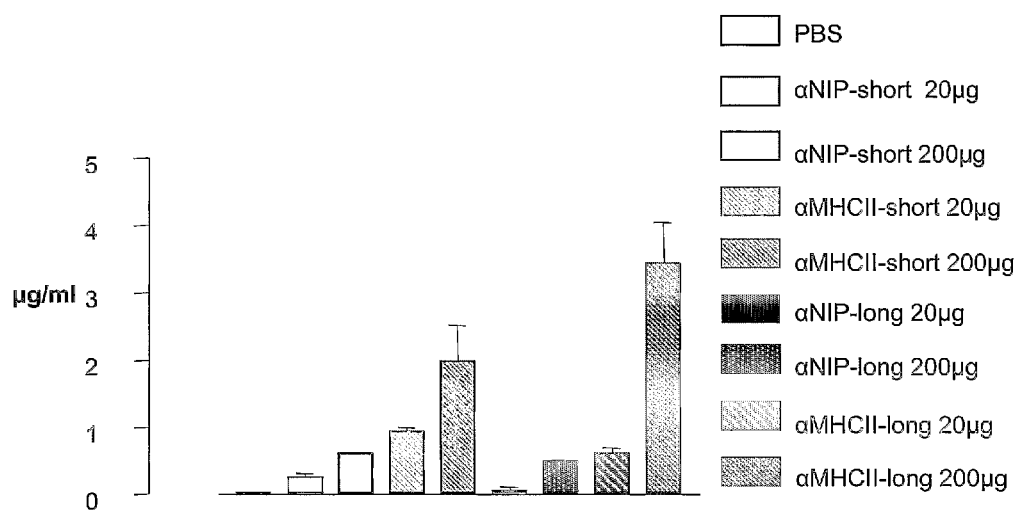
Fig 7 The MHC class II-specific Vaccibodies induce a strong anti-Id Ab response in the absence of adjuvants.

A Short hinge
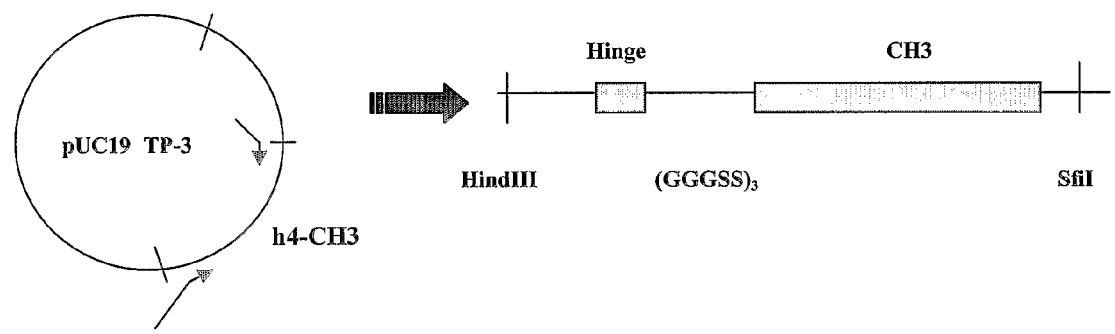
B long hinge
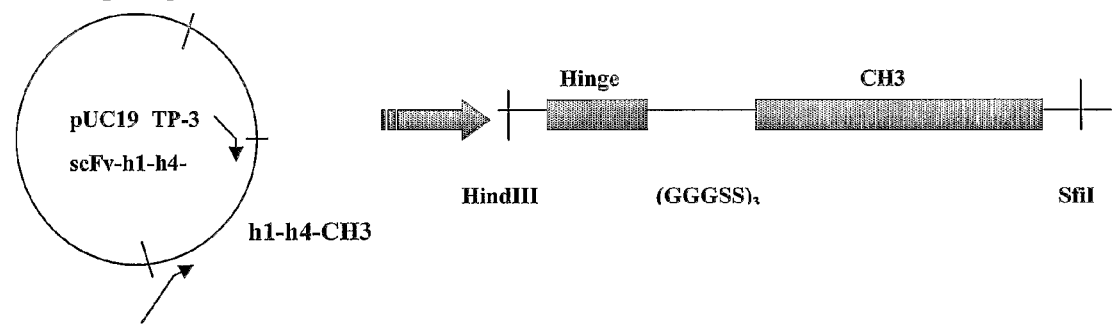
Fig 8 Construction of the two hinge-Cγ3 variants of hIgG3 origin by PCR.

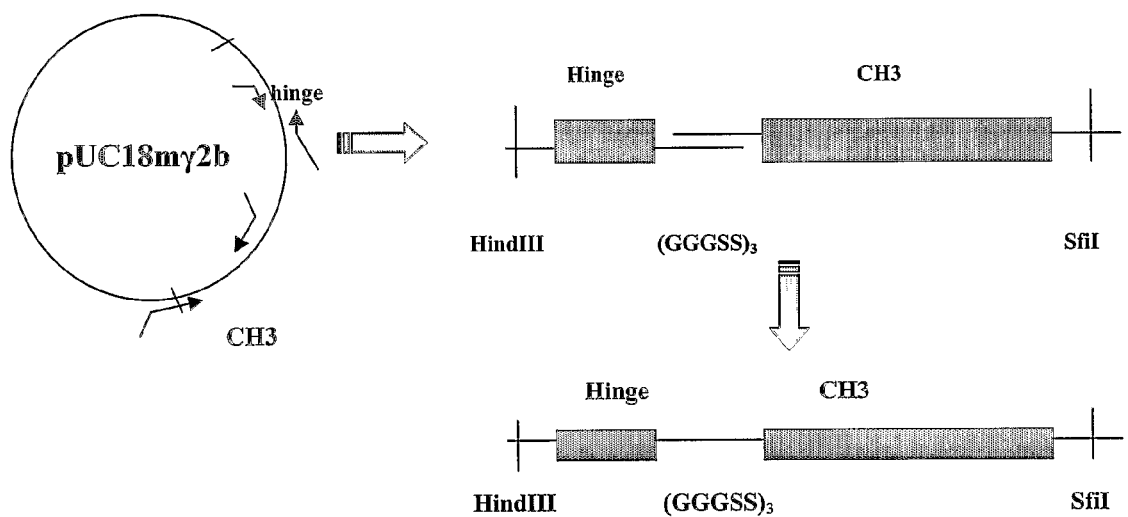
Fig 9 Construction of the hinge-Cγ3 segments derived from mIgG2b.

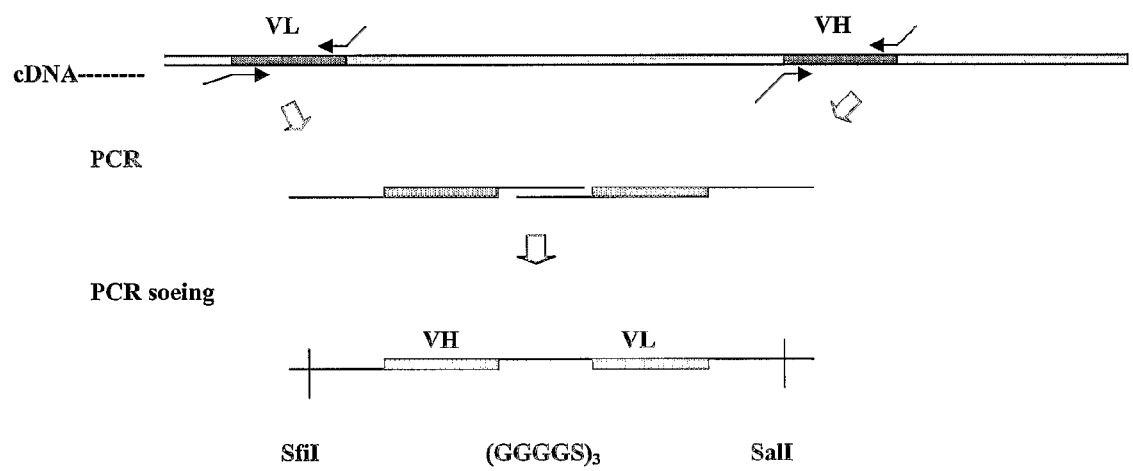
Fig 10 Construction of the scFv derived from the myeloma protein M315.

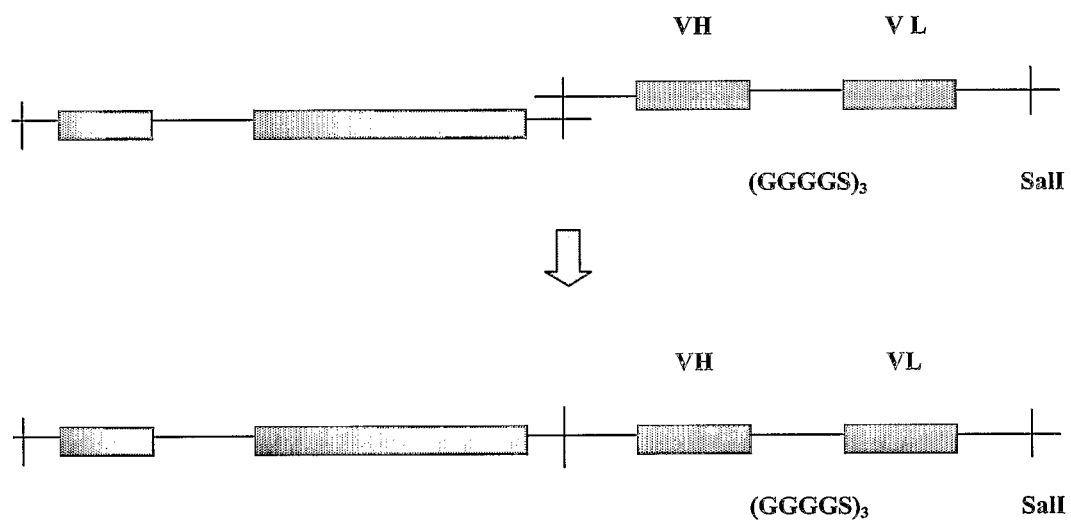
Fig 11 Joining of the hinge-Cγ3 segments and the M315 scFv by PCR soeing.

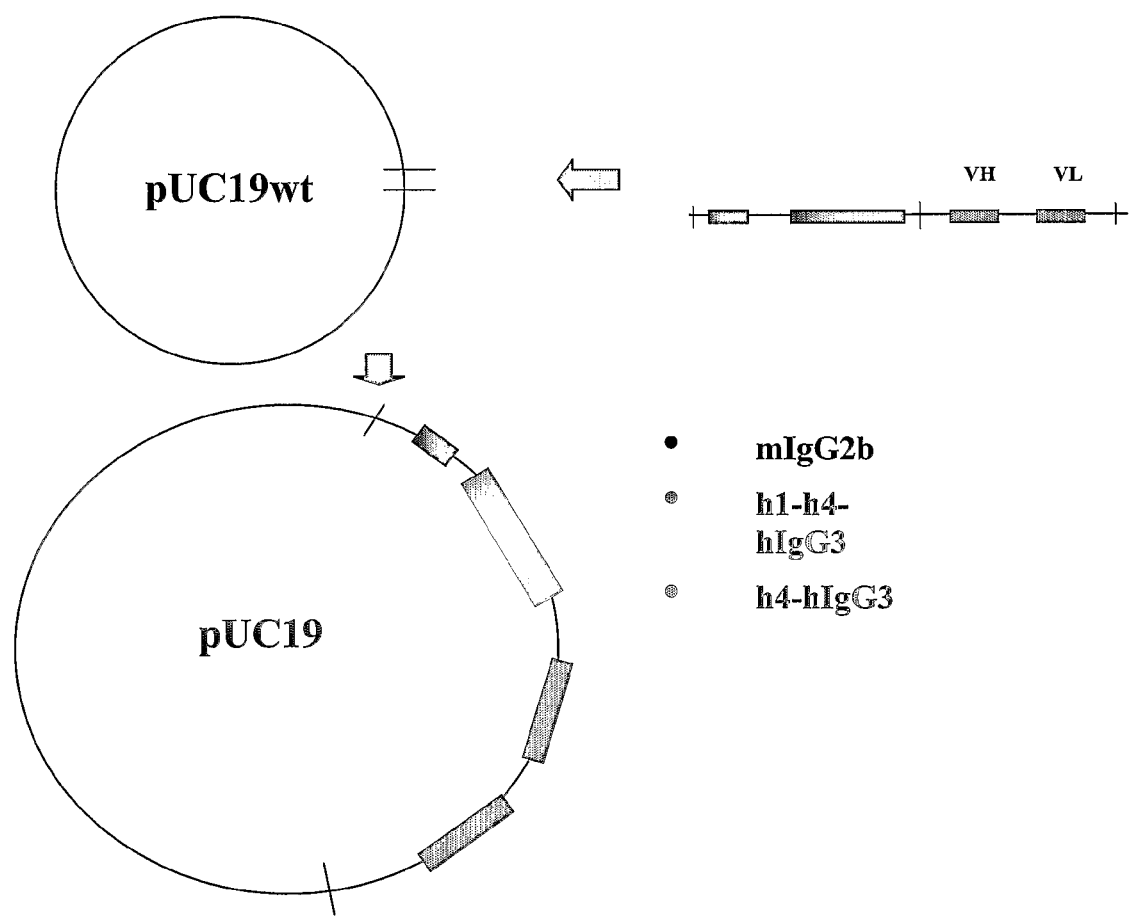
Fig 12 Subcloning of the hinge-Cγ3-M315 scFv into pUC19.

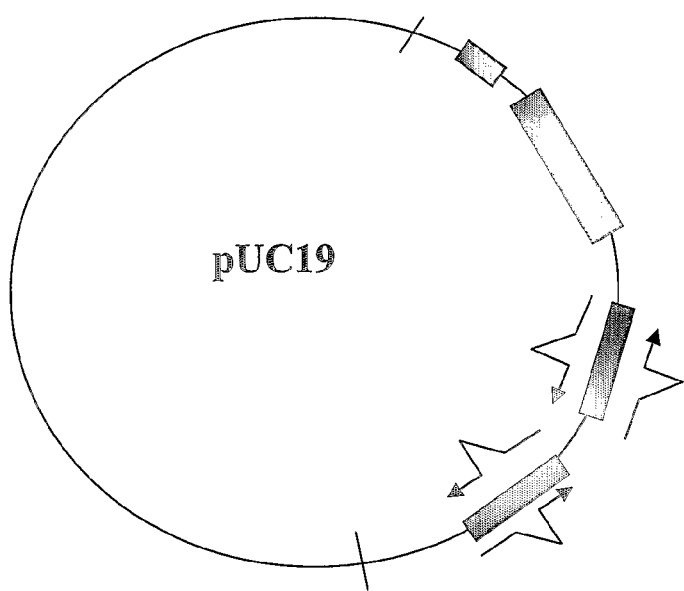
Fig 13 Removal of two inconvenient BamHI restriction enzyme sites by QuickChange PCR.

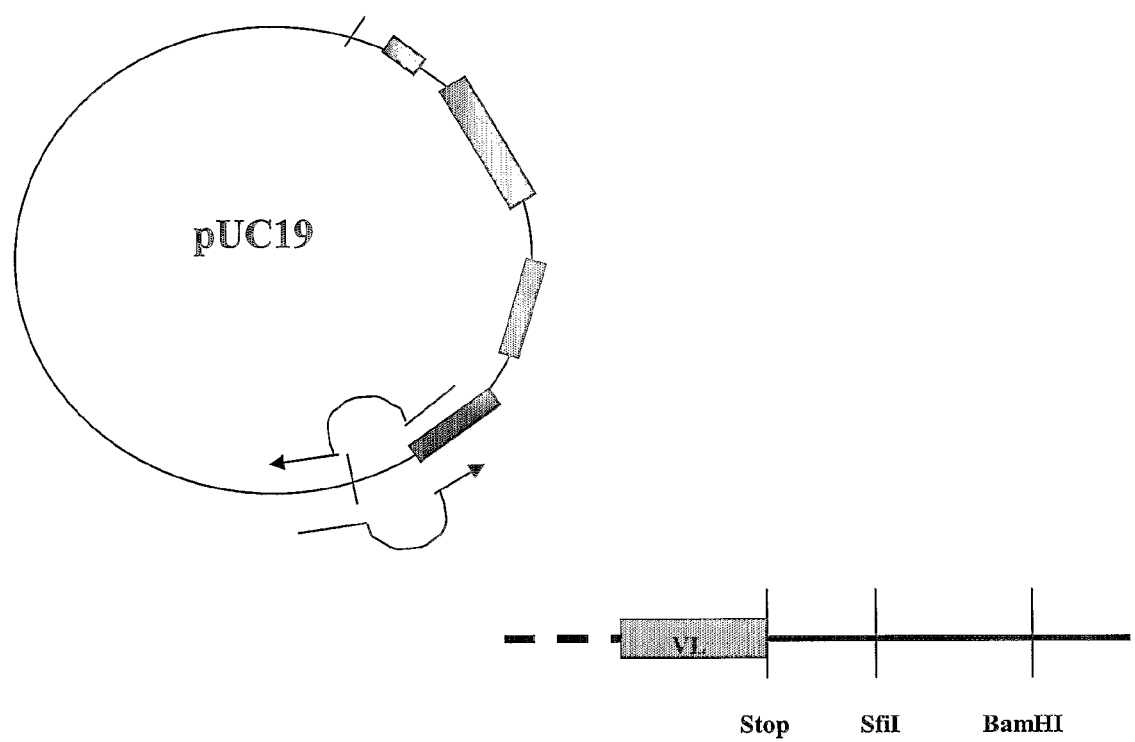
Fig 14 Introduction of stop codon, a SfiI and a BamHI restriction enzyme site downstream of the coding region by QuickChange PCR.

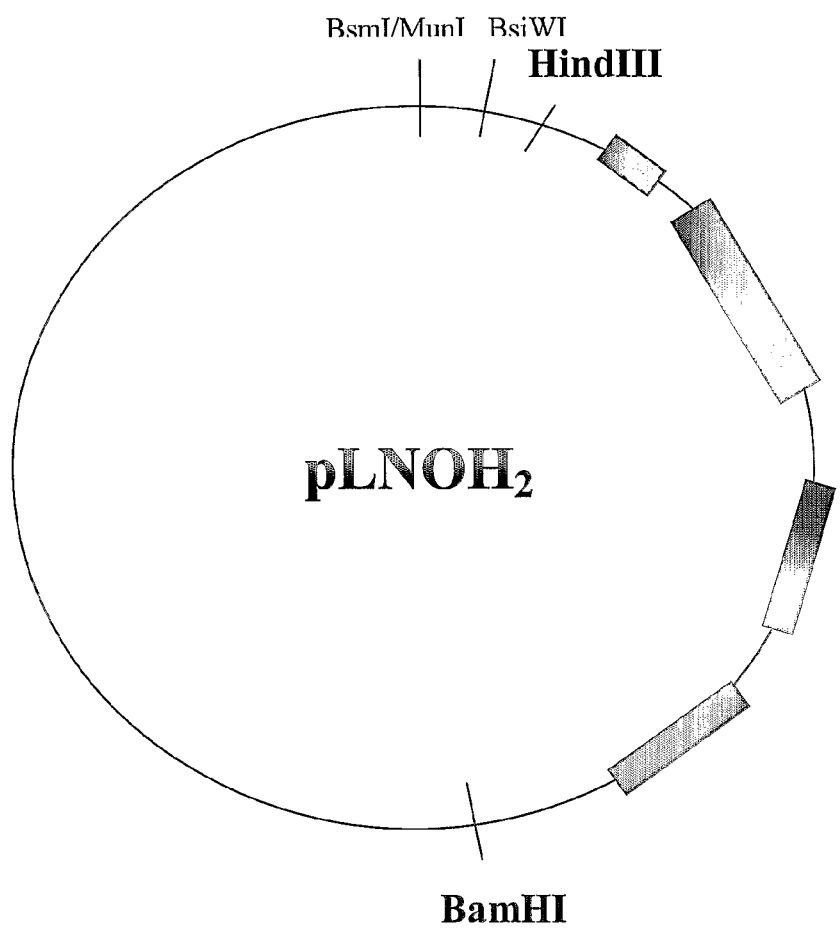
Fig 15 Subcloning into the C cassette of the expression vector pLNOH₂ on HindII-BamHI

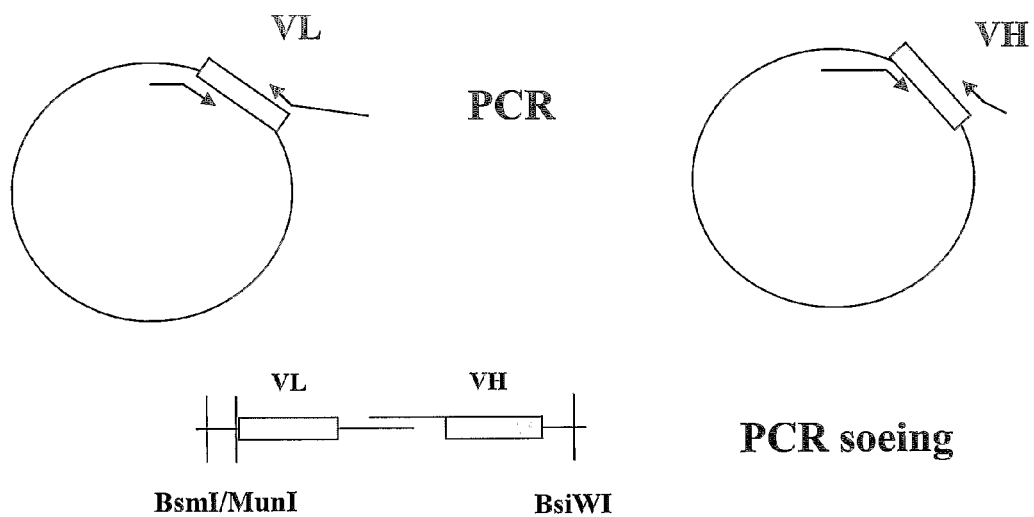
Fig 16 Cloning of the V regions specific for NIP and MHCII and assembling into a scFv format by PCR soeing.

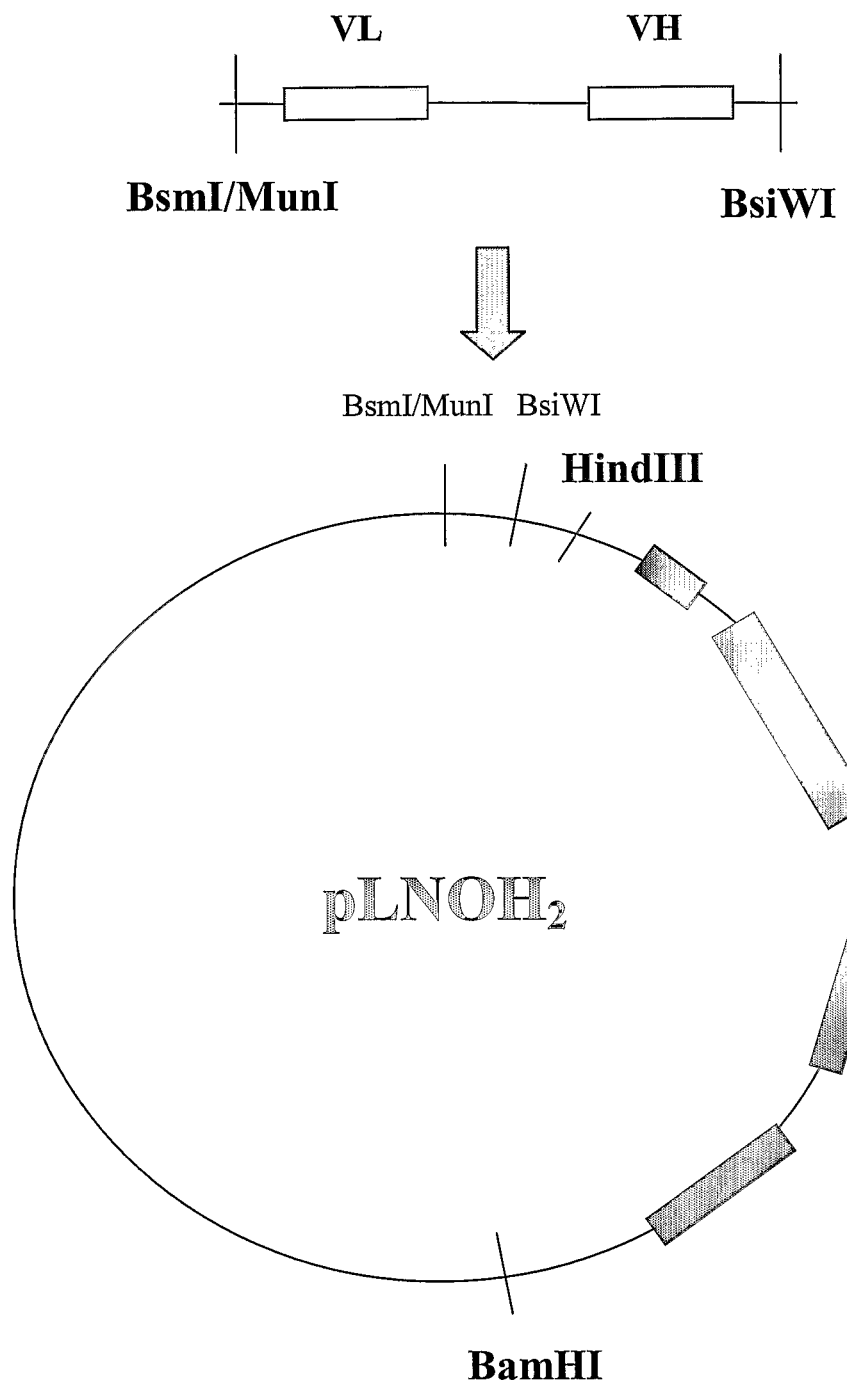
Fig 17 Subcloning into the expression vector pLNOH$_2$ on BsmI/MunI and BsiWI

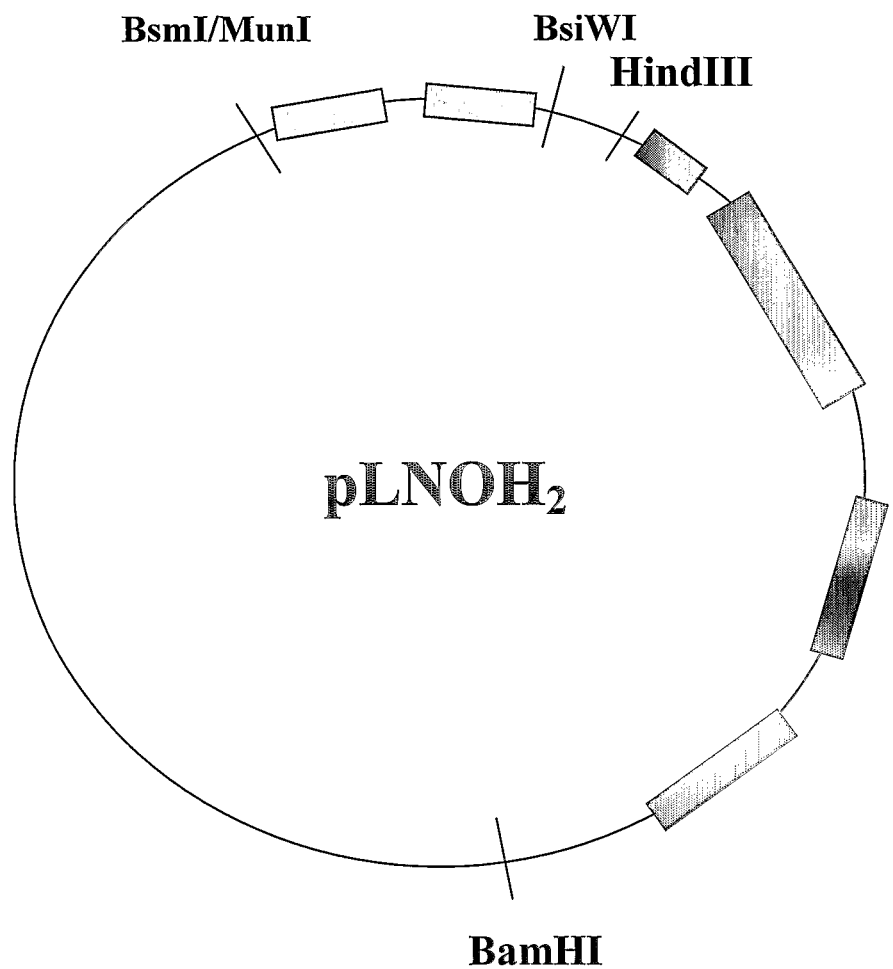
Fig 18 The final Vaccibody construct.

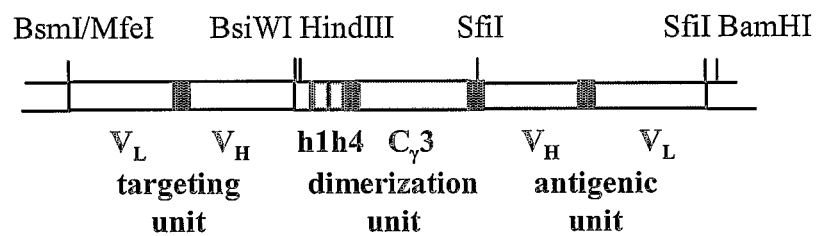
Fig 19 The Vaccibody gene construct

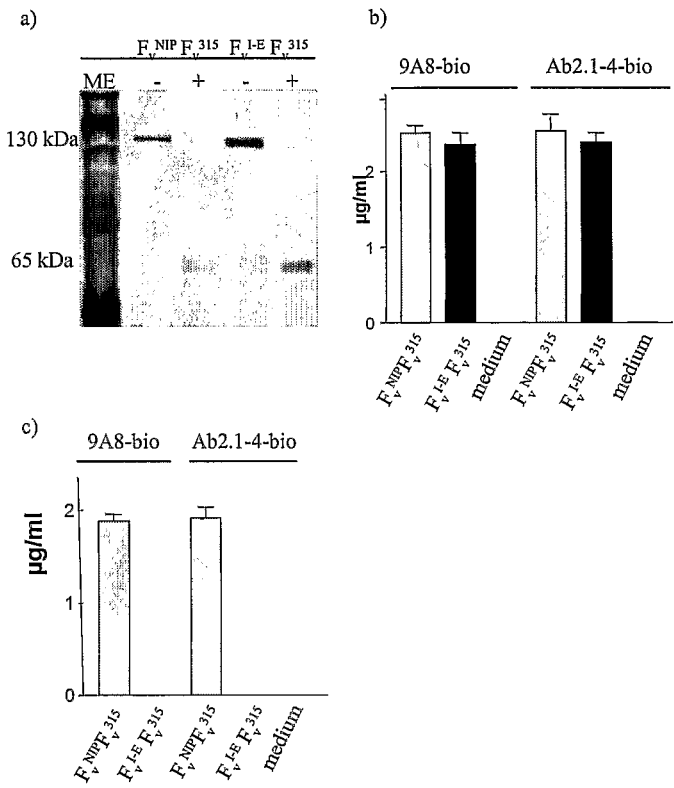
Fig 20 Vaccibodies are secreted as functional molecules.

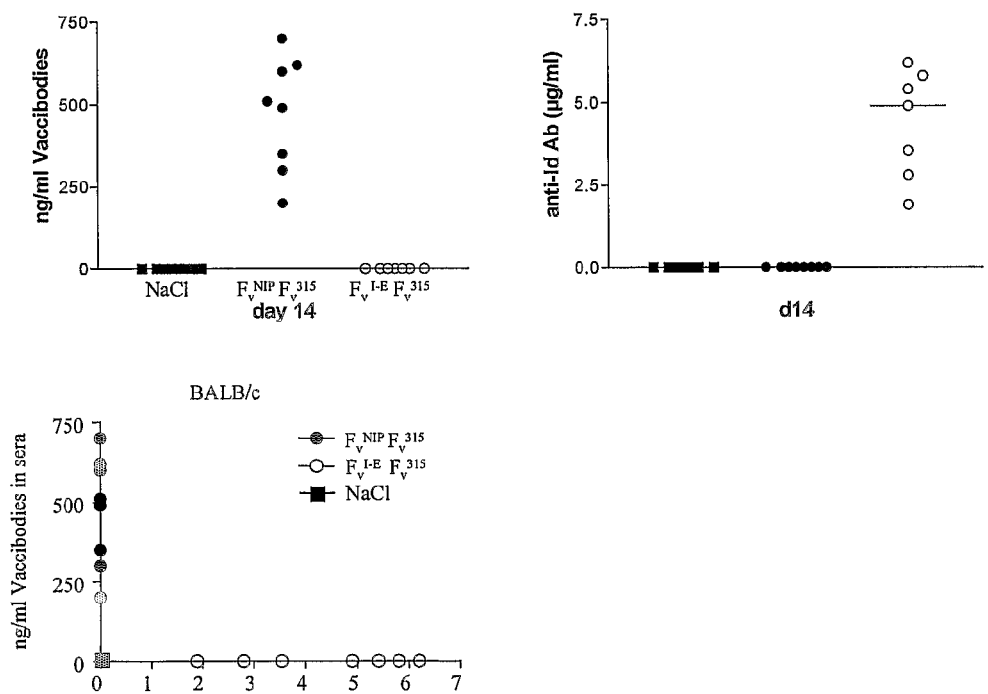
Fig 21 Production of Vaccibodies by intramucular injection of naked DNA plasmids followed by *in vivo* electroporation

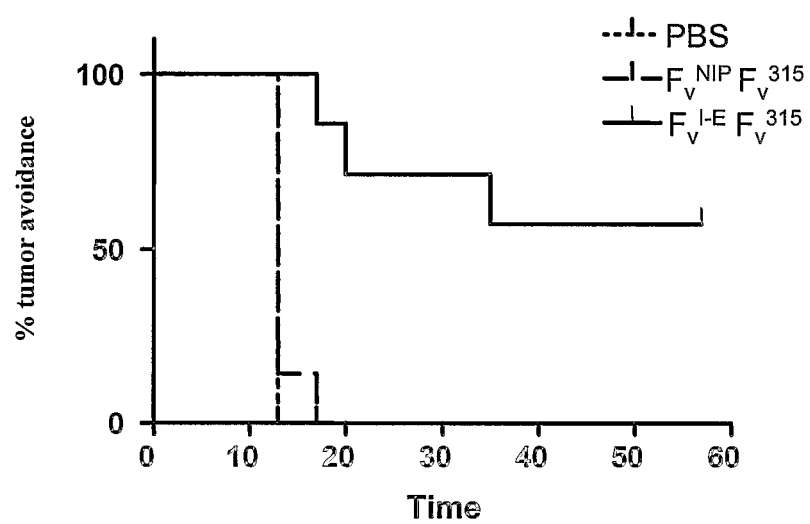
Fig 22 Tumor avoidance.

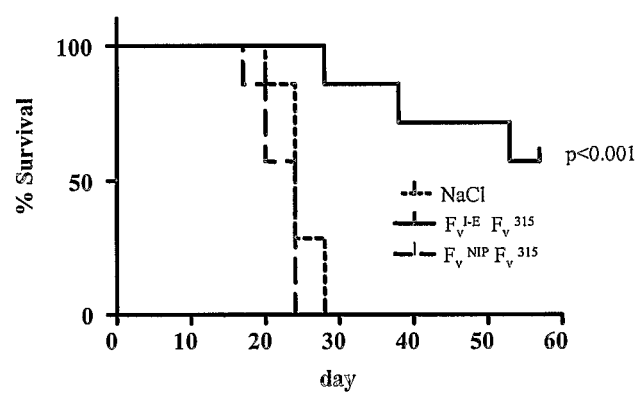
Fig 23 Induction of protective immunity against the MOPC315.4 plasmacytoma.

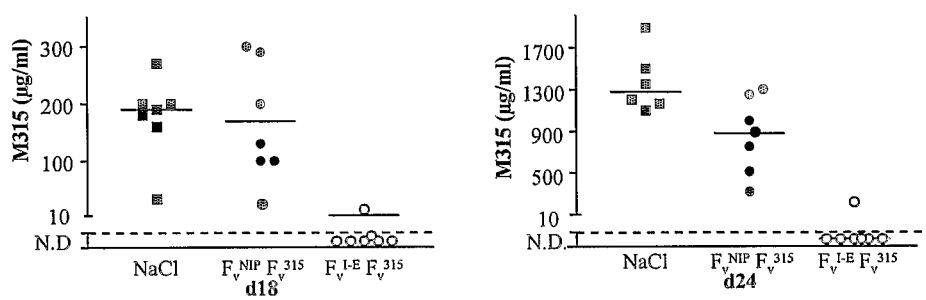
Fig 24 Level of M315 myeloma protein in sera of mice on a) day 18 and b) day 24 after MOPC315.4 challenge.

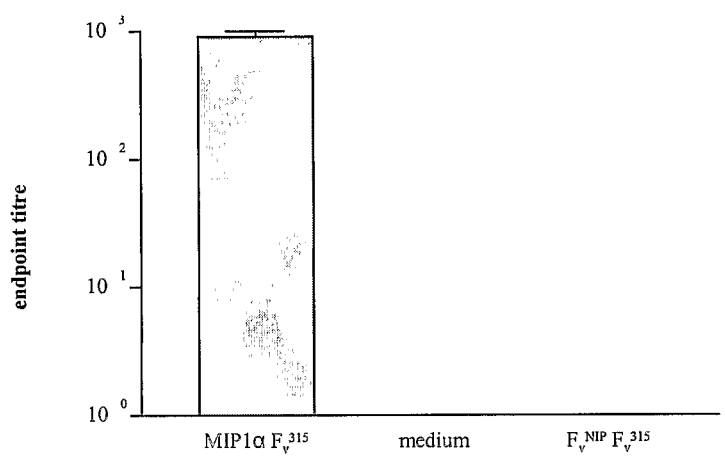
Fig 25 Chemokine Vaccibodies are secreted as functional molecules.

MODIFIED ANTIBODY

CROSS-REFERENCE TO RELATED APPLICATIONS

This application is a divisional of U.S. patent application Ser. No. 10/786,907 filed on Feb. 25, 2004 and PCT/NO2004/00051 filed Feb. 25, 2004 which claims the benefit of U.S. Provisional Application No. 60/450,134, filed Feb. 25, 2003. The entire disclosures of each of the above applications are incorporated herein by reference.

FIELD OF THE INVENTION

The present invention relates to a recombinant human antibody-based molecule called Vaccibodies, which are able to trigger both a T cell- and B cell immune response. More particularly, Vaccibodies by themselves induce such strong immune responses that adjuvants are not necessarily required. The present invention also relates to a method of treating e.g. multiple myeloma by means of the said Vaccibodies.

BACKGROUND OF THE INVENTION

Multiple myeloma (MM) is a bone marrow cancer in which a single plasma cell clone has turned malignant and produces monoclonal immunoglobulin (Ig). MM patients have a very poor prognosis. Although high response rates and increased survival can be achieved using high dose chemotherapy followed by autologous or allogeneic stem cell grafting, the majority of patients relapse and few, if any, are cured.

Myeloma cells produce monoclonal Ig that is unique for each tumor and thus for each individual patient. Ig is composed of two identical heavy (H) and two identical light (L) chains. L and H chains have highly diversified variable (V) regions, VL and VH. VL and VH together form the Fv (fragment variable) that contains unique antigenic determinants called idiotopes (Id). Idiotopes collectively constitute the idiotype of the Fv (of the Ig in casu). Induction of an immune response against the idiotype, so called Id-vaccination is a promising strategy in treatment of B cell lymphomas and MM (Bendandi, Gocke et al. 1999) (Tao and Levy 1993) (Huang, Wu et al. 2004) (Hakim, Levy et al. 1996) (King, Spellerberg et al. 1998) (Biragyn, Tani et al. 1999; Biragyn, Ruffini et al. 2002), and both anti-idiotypic antibodies (Sirisinha and Eisen 1971; Hough, Eady et al. 1976) and Id-specific T cells (Lauritzsen, Weiss et al. 1994) may be of importance. However, Id is a weak self-Ag in its original context (as part of Ig). Therefore, for vaccine purposes, it is important to enhance the immunogenicity of Id.

T helper cells (CD4+ T cells) recognize their antigen (Ag) after it has been processed through engulfment of foreign proteins by APC, proteolytic breakdown into peptide fragments that are loaded onto MHC class II molecules and transported to the surface of the APC where the peptide-MHC complex is presented to T cell receptors (TCRs) of CD4+ T cells. Activated CD4+ T cells stimulate cytotoxic T cells (CD8+ T cells) and B cells with the corresponding Ag specificity, initiating a broad response against the original Ag. A major problem concerning Id-vaccination of MM patients is that Id-specific CD4+ T cells in these patients, as extrapolated from experiments in mice [18], probably are tolerant to Id V-region determinants on the highly abundant myeloma protein. MM patients who have undergone autologous stem cell transplantation (ASCT) may be in an advantageous phase for Id-vaccination for the following two reasons: 1) relief from T cell tolerance to myeloma protein Id and 2) development of new T cells that can respond to Id-vaccination.

Targeting of T cell epitopes to surface molecules on APC with Troybodies (Lunde, Munthe et al. 1999), which are equipped with a T cell epitope incorporated in a loop in a constant Ig domain results in increased T cell stimulation by a factor of 100-100000 (Lunde, Rasmussen et al. 2001). However, Troybodies do not include the Ag in its native conformation, such as Fv, and are therefore restricted to induction of T cell responses. Therefore, to induce an anti-Id B cell response and anti-Id Abs, it is necessary to include the complete Fv of the M component of the patient. As for induction of an anti-Id T cell response, an inclusion of the entire Fv will greatly increase the chance of including idiotope sequences binding the patient's HLA-molecules, which is a prerequisite for activation of Id-specific T cells.

There have been several approaches for rendering idiotypes more immunogenic. Protein vaccination with complete Id+ immunoglobulins (Ig) fused with granulocyte-macrophage colony-stimulating factor (GM-CSF) (Tao and Levy 1993), or CD40 ligand (Huang, Wu et al. 2004) enhances the level of anti-Id antibodies and results in protection against B-cell lymphoma in mice. However, scFv-GM-CSF was effective only when injected as protein and not as a DNA vaccine (Hakim, Levy et al. 1996). On the other hand, DNA vaccination employing scFv fused to IL-1β did induce tumor immunity (Hakim, Levy et al. 1996). In another approach, scFv has been genetically fused with fragment C from tetanus toxin and delivered as a DNA vaccine by intramuscular (i.m.) injection. This strategy has resulted in increased levels of anti-Id antibodies, Id-specific CD4+ responses and protection against lymphoma a myelomas in mice. The mechanism of adjuvant activity of tetanus toxoid fragment C is unknown (King, Spellerberg et al. 1998). In a similar approach, scFv has been fused to chemokines like MCP3, IP10 mDF2β (Biragyn, Tani et al. 1999; Biragyn, Ruffini et al. 2002) and has been used both as a DNA and as protein vaccine (Biragyn, Tani et al. 1999). In several of these studies, foreign T cell epitopes corresponding to TT fragment-C or unique fusion sequences could have contributed to responses. Heightened anti-Id antibody responses and tumor protection has been observed. The mechanism of action of scFv-chemokine is unknown. One possibility is that the chemokine moiety targets Fv to chemokine receptors on APC for enhanced delivery of scFv. Alternatively, chemokines attract APC to the site of injection. However, both the Fragment C and chemokine fusion strategies rely on monovalent binding to their target molecules (King, Spellerberg et al. 1998; Biragyn, Tani et al. 1999). This is of concern because crosslinking has been shown to be of importance for optimal stimulation of T cells, e.g. for Troybodies (Lunde, Munthe et al. 1999).

With these considerations in mind, the inventors have designed a novel type of recombinant antibody-like molecules called Vaccibodies, a divalent molecule comprising a flexible hinge, with no FcR binding and that contain the Ag in its native conformation, with the purpose of inducing both strong Id-specific Ab and T cell responses. Vaccibodies are large and complex macromolecules, but, surprisingly, cells were able to produce and export intact molecules.

SUMMARY OF THE INVENTION

The present invention relates to a novel type of human recombinant antibody-like molecules useful in the treatment of i.e. multiple myeloma. These molecules, called Vaccibodies, bind APC and are able to trigger both T cell and B cell immune response. Moreover, Vaccibodies bind divalently to APC to promote a more efficient initiation of an immune response. Hence, a major purpose of the present invention is to induce a strong immune response to render adjuvants redundant. Vaccibodies comprise a dimer of a monomeric unit that consists of a scFv with specificity for a surface molecule on APC, connected through a hinge region and a Cγ3 domain to a scFv in the COOH-terminal end; the latter being of B cell lymphoma or myeloma origin (FIG. 1), although any origin is possible due to the cassette cloning system in the expression vector. The said molecule is capable of inducing an immune response against multiple myeloma, but extension to a general vaccination strategy for any polypeptide should be feasible. The present invention also relates to a DNA sequence coding for this recombinant antibody based molecule, to expression vectors comprising these DNA sequences, cell lines comprising said expression vectors, to treatment of mammals preferentially by immunization by means of Vaccibody DNA, Vaccibody RNA, or Vaccibody protein, and finally to pharmaceuticals and a kit comprising the said molecules.

BRIEF DESCRIPTION OF THE DRAWINGS

The present invention will become more fully understood from the detailed description and the accompanying drawings, wherein:

FIG. 1 The structure of the Vaccibody. The two scFvs in white target the Vaccibody to surface molecules on APC. They may be replaced by other targeting molecules, e.g. chemokine receptors. The hinge provides flexibility of the relative orientation of the two NH2-terminal scFvs and disulfide bridges the monomers. The CH3 domains (light grey) act as a spacer between the NH$_2$— and COOH terminal scFvs and participate in the dimerization through hydrophobic interactions. These dimerization motifs may be replaced by other dimerization or multimerization domains. The two scFvs shown in dark grey are the antigenic moiety of the Vaccibody. These scFvs are derived from the M component, thus harboring idiotypic sequences (black). The antigenic scFv may be replaced by any polypeptide derived from an antigenic source, conferring vaccine strategies towards any antigen.

FIG. 2 Principle. The Vaccibody is targeted to surface molecules on APC, the complex is taken up by receptor-mediated endocytosis, processed and Id-peptides are presented to CD4+ T cells on MHC class II. Simultaneously, the Id may stimulate B cells with an anti-Id BCR. These B cells will also serve as APC for the CD4+ T cells. Thus, T and B cells will cooperate to enhance the response, as indicated. Anti-Id B cells will as a consequence develop into plasma cells that produce anti-Id antibodies.

FIG. 3 The MHC class II-specific Vaccibodies bind CD19$^+$ splenocytes (white). The NIP-specific Vaccibodies (negative controls—grey), do not bind to the splenocytes. Binding was detected with streptavidinPE and 9A8bio which is a rat mAb that binds the antigenic Fv of M315 origin (Vλ1/2).

FIG. 4 The NIP-specific control Vaccibodies exhibits binding to the hapten NIP. Supernatant from cells transfected with genes encoding NIP-specific Vaccibodies was added to ELISA plates coated with NIP-BSA. 9A8 bio (antiVλ1/2) was used as the secondary Ab. Similar results were obtained with a biotinylated anti IdAb (Ab2.1-4 bio).

FIG. 5 The Vaccibodies exhibit binding to DNP, hence the antigenic scFv is correctly folded. The M315 Ab, from which the antigenic scFv is derived, is specific for the hapten DNP. ELISA plates were coated with DNP-BSA. Supernatants from cells transfected with genes encoding various Vaccibodies were added. Binding was detected with 9A8 bio.

FIG. 6 APC pulsed with titrated amounts of MHC class II specific Vaccibodies stimulated polarized M315-specific T cells from TCR-transgenic SCID mice >100-1000 fold better than the NIP-specific, untargeted control Vaccibodies. There were no significant differences between the Vaccibodies with a long sequence prior to the first disulfide bridge in the hinge (h1+h4) compared to the Vaccibodies with a short hinge sequence above the first disulfide bridge (h4).

FIG. 7 The MHC class II-specific Vaccibodies induce a strong anti-Id Ab response in the absence of adjuvant. BALB/c mice were injected with Vaccibodies, 20 μg and 200 μg, respectively. Blood samples were taken on different time points for sera analysis. Shown is data from sera taken on day 28, 14 days after the second immunization of Vaccibodies. The MHC class II-specific Vaccibodies induced a strong anti-Id Ab response. The Vaccibodies with the longest hinge (h1+h4) induced the strongest anti-Id Ab response reaching 3-4 μg/ml in sera.

FIG. 8 Construction of the two hinge-Cγ3 variants derived from hIgG3 by PCR. The templates were from pUC19 containing modified hIgG3 constant regions were the h4 exon were connected to the CH3 domain (A) or the h1 exon were connected to the h4 exon further connected to the CH3 domain (B) (Olafsen T et al, 1998). The primers inserted HindIII (5') and SfiI (3') restriction enzyme sites. The hinge and CH3 domain are connected by a triplicate of the amino acids GlyGlyGlySerSer.

FIG. 9 Construction of the hinge-Cγ3 segments derived from mIgG2b. The hinge and the CH3 genes were amplified from a pUC18 vector containing the constant region of mIgG2b by PCR with two primers encoding a HindIII (5') and a SfiI (3') restriction enzyme site. The two PCR fragments were joined by PCR SOEing. In this reaction, the hinge and CH3 domain were connected by a triplication of the amino acids Gly-Gly-Gly-Ser-Ser.

FIG. 10 Construction of the scFv derived from the myeloma protein M315. The cDNA that functioned as a template in the PCR reactions were derived from mRNA extracted from MOPC315.4 cells. The V regions were joined by PCR SOEing resulting in a scFv. In this reaction, the V regions were connected by a triplicate of GlyGlyGlyGlySer. Furthermore, the gene fragments encoding the complete scFv were flanked by SfiI and SalI restriction enzyme sites.

FIG. 11 Joining of the hinge-Cγ3 segments and the M315 scFv by PCR SOEing. This reaction introduced the SfiI site 5' of the antigenic scFv encoding region.

FIG. 12 Subcloning of the hinge-Cγ3-M315 scFv into pUC19. Three different dimerization motifs were included, derived from mIgG2b or IgG3. In all cases, they consisted of hinge followed by a triplicate of GlyGlyGlySerSer and CH3. Two different hinges were derived from hIgG3, one consisting of h1 linked to h4, and one consisting of h4, only.

FIG. 13 Removal of two inconvenient BamHI restriction enzyme sites within the gene fragment encoding the antigenic scFv by QuickChange PCR.

FIG. 14 Introduction of stop codon, a SfiI and a BamHI restriction enzyme site downstream of the coding region by QuickChange PCR.

FIG. 15 Subcloning into the C cassette of the expression vector pLNOH$_2$ on HindIII-BamHI.

FIG. 16 Cloning of the V regions specific for NIP and MHCII. The V regions were amplified and joined by PCR soeing resulting in scFvs. The linker connecting the V regions consists of a triplicate of GlyGlyGlyGlySer. The gene fragments encoding the complete scFvs are flanked by BsmI/

MunI and BsiWI sites. Linkers and restriction sites were introduced in the PCR reactions.

FIG. 17 Subcloning into the expression vector pLNOH2 on BsmI/MunI and BsiWI.

FIG. 18 The final Vaccibody construct.

FIG. 19 Detailed figure of Vaccibody gene construct. The targeting unit is inserted between the BsmI/MfeI and BsiWI restriction enzyme sites (The V cassette of the pLNOH$_2$ vector). The hinge-Cγ3-Fv315 is inserted between the HindIII and BamHI sites into the C cassette of pLNOH2. The hinge and the Cγ3 domain as well as the two scFv's are connected with $(G_4S)_3$ linkers (black boxes). The Cγ3 and the $Fv^{315}$ are connected through a GLSGL linker. The $Fv^{315}$ is inserted between two nonidentical SfiI restriction enzyme sites. The antigenic unit and dimerization motif may be of any origin appropriate. Also, functional fragments of Cγ3 may be employed, or a sequence which is substantially homologous to the Cγ3 sequence or Cγ3 fragments.

FIG. 20 Vaccibodies are secreted as functional molecules. Two distinct Vaccibodies were tested, one carrying the hapten specific $Fv^{NIP}$ as targeting unit, while the other carried the MHC class II-specific $Fv^{I-E}$ as targeting unit. Both carried the scFv from M315 ($Fv^{315}$) as antigenic unit. a) 10% SDS-PAGE of metabolically labeled Vaccibodies immunoprecipitated from culture supernatants of transfectants with or without reduction of disulfide bonds by mercaptoethanol (ME). b) DNP-specificity of the Vaccibodies was measured by ELISA. Supernatants from NSO cells transfected with Vaccibodies were added to ELISA plates coated with DNP-BSA. Data are illustrated as mean of triplicates and error bars indicate SEM. c) NIP-specificity was measured by ELISA. ELISA plates were coated with NIP-BSA. Vaccibodies in both b) and c) were detected by either 9A8-bio ($\alpha V\lambda 1/2$) or Ab2.1-4 (specific for Id of $Fv^{315}$) $Fv^{315}$ carries $V\lambda 2$ and FvNIP carries $V\lambda 1$ and will both bind 9A8 mAb. Only $Fv^{315}$ will bind Ab2.1-4 mAb. $Fv^{I-E}$ carries Vκ and will bind neither of the mAbs.

FIG. 21 Production of Vaccibodies by intramucular injection of naked DNA plasmids followed by in vivo electroporation. Serum samples were collected on day 14. Vaccibody plasmids were injected into I-$E^d$ positive BALB/c mice, which were subsequently electroporated. a) Level of Vaccibodies in sera was measured by ELISA, with DNP-BSA and 9A8bio as described previously. b) The same day 14 sera samples were analyzed for anti-Id antibodies by ELISA. Microtiter plates were coated with M315 and 187-bio (anti-mouse κ Ab) was used for detection. c) Comparison of detectable Vaccibody levels and anti-Id antibodies. The amount of detectable Vaccibodies in sera is shown on the y-axis and the level of αId-Abs is shown on the x-axis.

FIG. 22 Tumor avoidance. BALB/c mice were immunized once with naked plasmids encoding MHC class II specific Vaccibodies ($Fv^{I-E} Fv^{315}$), nontargeted NIP-specific Vaccibodies ($Fv^{NIP} Fv^{315}$) or 0.9% NaCl by i.m. immunization into the two quadriceps muscles (25 μg/muscle) followed by in vivo electroporation. They were challenged with 1.6×10$^5$ MOPC315.4 myeloma cells s.c. and the first day tumor take were recorded. A tumor of >3 mm was scored as positive tumor take.

FIG. 23 Induction of protective immunity against the MOPC315.4 plasmacytoma. BALB/c mice were immunized once with naked plasmids encoding MHC class II specific Vaccibodies ($Fv^{I-E} Fv^{315}$), nontargeted NIP-specific Vaccibodies ($Fv^{NIP} Fv^{315}$) or 0.9% NaCl by i.m. immunization into the two quadriceps muscles (25 μg/muscle) followed by in vivo electroporation. They were challenged with 1.6×105 MOPC315.4 myeloma cells s.c. and their survival were compared.

FIG. 24 Level of M315 myeloma protein in sera of mice on a) day 18 and b) day 24 after MOPC315.4 challenge in BALB/c mice vaccinated i.m. with Vaccibody plasmids followed by in vivo electroporation. M315 in sera samples were measured by ELISA coated with anti-Id-mAb (Ab2.1-4) and detected by biotinylated anti-IgA mAb (8D2).

FIG. 25 Chemokine Vaccibodies are secreted as functional molecules. MIP-1α $Fv^{315}$ has mouse macrophage inflammatory protein 1α as the targeting unit and scFv from M315 ($Fv^{315}$) as the antigenic unit. Functionality of MIP-1α in Vaccibody format was measured in ELISA. Supernatants from 293E cells transfected with Vaccibodies were added to ELISA plates coated with anti-mouse MIP-1α mAb (R&D Systems) and detected by 9A8-bio ($\alpha V\lambda 1/2$).

DETAILED DESCRIPTION OF THE PREFERRED EMBODIMENTS

The following description of the preferred embodiment(s) is merely exemplary in nature and is in no way intended to limit the invention, its application, or uses.

The present invention relates to a recombinant human antibody-based molecule, called Vaccibodies, comprising dimers of a monomeric unit that consist of a single chain fragment variable (scFv) of immunoglobulins (Ig) with specificity for surface molecules on Ag presenting cells (APC), connected through a hinge region and a Cγ3 domain to a scFv in the COOH-terminal end, the latter being derived from a myeloma protein (FIG. 1), although any origin is possible due to the cassette cloning system of the expression vector. The hinge region and the Cγ3 domains (carboxyterminal C domain of Ig) contribute to dimerization of the Vaccibody through disulfide bridges in the hinge and strong hydrophobic interactions between the two Cγ3 domains. Hence, the dimeric product will include two preferably identical scFvs with binding specificity for the same surface molecules on APC (FIG. 2), enabling bivalent binding. Bivalent binding (i.e. crosslinking) is of importance to trigger activation of the target cell and thereby initiation of an immune response. Also, bivalent binding provides increased binding strength due to avidity effects, and increases the likelihood of receptor mediated endocytosis into the APC and subsequent degradation inside the APC. Furthermore, the bivalent binding may provide important receptor mediated intracellular signaling to the APC. The scFvs with a targeting function are either derived from B cell hybridomas expressing monoclonal antibodies (mAbs) that bind to surface molecules on APC, or they may be derived from any source, e.g. phage display libraries. The use of scFvs from B cell hybridomas as the targeting moiety opens for a great range of possible targets due to the large collection of B cell hybridomas that produce mAbs which bind different surface molecules on APC. Furthermore, one may choose the nature of the signal given to the targeted cell by employing agonistic or antagonistic mAbs. Growing knowledge of Ab-Ag interactions will allow the improvement of the binding affinity of such mAbs to their Ag by amino acid replacements in the binding sites. This can be performed by ordinary site-directed mutagenesis. For vaccine purposes, an attractive approach is to target the Vaccibodies to surface molecules expressed exclusively on subsets of dendritic cells (DC) that are able to initiate a strong, specific immune response towards the patients own Id. Examples of such target surface molecules on APC are CD40, Toll-like receptors and chemokine receptors. Because the targeting scFv is inserted into the V cassette of the expression vector pLNOH2 (Norderhaug, Olafsen et al. 1997), it is easily exchanged with other scFvs (FIG. 17).

The crucial dimerization motifs in the Vaccibodies constructed in the examples so far, include hinge regions and Cγ3 domains. The hinge contributes to the dimerization through the formation of interchain disulfide bridges. In addition, it functions as a flexible spacer between the domains allowing the two scFvs with targeting tasks to bind simultaneously to two target molecules expressed with variable distances (FIG. 2). The C☐3 domains contribute to the dimerization through hydrophobic interactions. These dimerization motifs can be exchanged with other multimerization moieties (e.g. from other Ig isotypes/subclasses).

The C-terminal scFv derived from the monoclonal Ig produced by myeloma or lymphoma cells, also called the myeloma/lymphoma M component, can be genetically exchanged with other scFvs or any antigen because the vector has been constructed with a Sfi I restriction site (FIG. 8). Therefore, the scFv derived from the model myeloma protein used in the present example is easily swapped with scFv from the M component of any patient with B cell lymphoma or multiple myeloma. Thus, this vector will allow for rapid construction of individual patient specific vaccines. The dimeric structure of the Vaccibody not only affords crosslinking, but should also allow double loading of the patient Fv to the APC per Vaccibody molecule compared to a single scFv combined to a single targeting moiety. Furthermore, there is in a single Vaccibody duplication of serological idiotypic determinants, which might be of importance for the anti-Id B cell response. The Vaccibodies lack a CH2 domain and hence all FcR binding sites, and should therefore exclusively be taken up through its target molecules, such as MHC class II in the example used and not by any FcRs, ensuring that a large proportion of the vaccine will arrive at the intended target cells. This is in contrast to vaccines that exert their effect through the binding to an FcR on a target cell (Ravetch and Bolland 2001).

Vaccibodies can be extended to a general medical treatment through induction of an immune response against any polypeptide of any origin. It is possible to replace the idiotypic scFv with other antigenic sequences of sufficient length to allow proper folding of the polypeptide. This sequence may be derived from other cancer proteins or infectious agents. Insertion of such a sequence in a Vaccibody format might also lead to activation of both arms of the immune response, similar to the Vaccibodies that are described herein, which comprise the idiotypic scFv. Immunization by means of Vaccibody protein, Vaccibody DNA, or Vaccibody RNA, the latter two executed e.g. by intramuscular injection followed by electroporation (See Examples), are all feasible methods.

The scFvs on the NH2-terminal end of the Vaccibodies target the Vaccibodies to APC through binding to surface molecules (FIG. 2), and in the example shown they bind to MHC class II. MHC class II is expressed on all professional APC, so the Vaccibodies described herein are able to target B cells, DC and macrophages. Targeting of conventional Ag-Ab complexes to MHC class II induces activation of specific CD4+ T cells (Snider and Segal 1987; Casten and Pierce 1988). Targeting of Troybodies to MHC class II has previously been shown to enhance Ag presentation and T cell activation in vitro as well as in vivo (Lunde, Western et al. 2002). In the antigenic region of the molecule, the Vaccibodies of the examples contain the scFv of the myeloma protein M315 derived from the BALB/c plasmacytoma MOPC315.4. The λ2315 light chain of M315 harbors three defined somatic mutations in the CDR3 loop and functions as a model idiotypic T cell epitope in a well defined system (Bogen, Malissen et al. 1986; Bogen and Lambris 1989).

The Vaccibodies have been genetically assembled, and the DNA transfected into NSO cells, 293E cells and Cos-7 cells. Transfectants produce and secrete the recombinant Vaccibody molecules. The targeting scFvs at one end of the Vaccibodies exhibit binding to MHC class II (FIG. 3). The antigenic scFv at the other end of the Vaccibody binds DNP (di-nitro-phenyl, the specificity of M315) (FIG. 5). Thus, both the targeting and antigenic scFvs retain the same folding pattern as in their original context. We have evidence that Vaccibodies have the ability to induce strong T cell responses through their binding to APC and presentation of Id-peptides on class II molecules to Id-specific CD4+ T cells in vitro (FIG. 6). Furthermore, since they have intact Fv of the M-component, they elicit anti-Id antibodies in significant amounts in vivo when injected into BALB/c mice without adjuvants (FIG. 7).

To determine if MM patients treated with ASCT achieve remission with a low serum myeloma protein concentration, ELISA should performed for each patient's myeloma protein because routine assays (agarose gel electrophoresis, combined with immunofixation) have only a sensitivity of about 0.2-1 mg/ml, which is far too insensitive. The kinetic data of the serum myeloma protein levels will indicate if and when Id-vaccination may best be performed post ASCT to avoid the problem of T cell tolerance of newly educated thymic emigrants. To achieve this, mice are immunized with DNA encoding patient specific Vaccibodies by in vivo electroporation of muscle cells. Sera from immunized mice are absorbed on anti human Ig-Sepharose to remove crossreactive antibodies and thereafter eluted to obtain purified highly Id-specific antibodies. Sandwich ELISAs specific for each patient's myeloma are performed as follows: The purified anti-Id Ab from mice is coated in wells. Serum from the patient in casu is added. Myeloma protein binding to anti-Id antibodies will be detected by use of Ab specific for human IgG or IgA. The sensitivity of such sandwich ELISAs is usually <1 ng/ml, which is >106 times more sensitive than routine assays. Furthermore, to monitor development of new T cells, profile of T cells in blood will be monitored by flow cytometry with Vβ-specific mAbs, in combination with other markers.

The present invention relates to a pharmaceutical comprising the above described recombinant based antibody, DNA/RNA sequences, or expression vectors according to the invention. Where appropriate, this pharmaceutical additionally comprises a pharmaceutically compatible carrier. Suitable carriers and the formulation of such pharmaceuticals are known to a person skilled in the art. Suitable carriers are e.g. phosphate-buffered common salt solutions, water, emulsions, e.g. oil/water emulsions, wetting agents, sterile solutions etc. The pharmaceuticals may be administered orally or parenterally. The methods of parenteral administration comprise the topical, intra-arterial, intramuscular, subcutaneous, intramedullary, intrathekal, intraventricular, intravenous, intraperitoneal or intranasal administration. The suitable dose is determined by the attending physician and depends on different factors, e.g. the patient's age, sex and weight, the kind of administration etc. The present invention also relates to a kit comprising Vaccibody DNA, RNA, or protein for diagnostic, medical or scientific purposes.

The above described nucleotide sequences may preferably be inserted into a vector suited for gene therapy, e.g. under the control of a specific promoter, and introduced into the cells. In a preferred embodiment the vector comprising said DNA sequence is a virus, e.g. an adenovirus, vaccinia virus or an adeno-associated virus. Retroviruses are particularly preferred. Examples of suitable retroviruses are e.g. MoMuLV or HaMuSV. For the purpose of gene therapy, the DNA/RNA sequences according to the invention can also be transported to the target cells in the form of colloidal dispersions. They comprise e.g. liposomes or lipoplexes.

In a preferred embodiment of the present invention naked Vaccibody DNA construct is injected intra-muscularly into mice, whereupon the site of injection is subject to in vivo electroporation. This DNA vaccination resulted in production of Vaccibody protein which conferred life-saving protective immunity on a majority of the mice.

Materials and Methods

Mice

BALB/cABom were from Bomholtgaard (Ry, Denmark). The λ2315-specific TCR-transgenic mice on a BALB/c background (Bogen, Gleditsch et al. 1992) were bred in our animal facility.

Cell Lines

The 14-4-4S Hybridoma (Ozato, Mayer et al. 1980) and NSO cells were purchased from American Type Culture Collection (ATCC, Manassas, Va.). 293E cells, a variant of the 293 cell line expressing the Epstein-Barr virus EBNA1 protein.

Construction of Vaccibodies

The gene for the hIgG3 hinge and CH3 domain was cloned from the pUC19 vector containing hinge genetically combined with Cγ3 genes of the hIgG3 subclass (Olafsen, Rasmussen et al. 1998). Two variants of the hinge length in the humanized Vaccibodies were made; one with just the h4 exon connected to the CH3 domain (sh) and one with both exon h1 and h4 connected to the CH3 domain (lh) (FIG. 8). The primers included restriction enzyme sites (underlined): 5' h4: tagcaagcttgg cca gcg cag gga g; 3'CH3: caggccaccgaggcc ttt acc cgg aga cag gga. The h1 exon were introduced directly upstream of the h4 exon by QuickChange PCR using these primers Qh1a: ctccaatcttctctctgca gag ctc aaa acc cca ctt ggt gac aca act cac aca gag ccc aaa tct tgt gac ac and Qh1b: gt gtc aca aga ttt ggg ctc tgt gtg agt tgt gtc acc aag tgg ggt ttt gag ctc tgcagagagaagattgggag.

The murine Vaccibodies have a complete hinge and CH3 domain of the mIgG2b subclass picked up by PCR from a pUC18 vector containing the Cγ2b genes (FIG. 9). The primers included restriction enzyme sites (underlined) or linkers (bold) with the complementary sequences (italic): 5' hinge: tagcaagctt ca gag ccc agc ggg ccc; 3' hinge: 5' tcc acc tcc gct gct tcc acc gcc tgg gca ttt gtg aca ctc ctt g; 5'CH3: gga agc agc gga ggt gga agt gga ggg cta gtc aga gct cca ca; 3'CH3: ca ggccaccgaggcc acc cgg aga ccg gga gat g. The hinge and the CH3 domain were then joined by PCR SOEing.

The Antigenic V region genes were cloned from the plasmacytoma MOPC315.4 (Eisen, Simms et al. 1968). The V regions were obtained by extracting mRNA from the MOPC315.4 cell line with oligo (dT)-coated magnetic Dynabeads (Dynal). First strand cDNA were then made and used as template for PCR amplification of the V region genes using specific primers annealing to the exact ends of the M315 V region sequences. The primers included restriction enzyme sites (underlined) or linkers (bold) with the complementary sequences (italic). The primer sequences were: 5'VH: ggcctcggtggcctg gat gta cag ctt cag gag tca; 3'VH: gcc aga gcc acc tcc gcc aga tcc gcc tcc acc tga gga gac tgt gag agt ggt; 5'VL: ggc gga ggt ggc tct ggc ggt ggc gga tcg cag gct gtt gtg act cag gaa; 3'VL: gacgtcgac tag gac agt gac ctt ggt tcc. The VH and VL genes were then joined by PCR soeing to a scFv format (FIG. 10).

The complementary sequences in the tags 3' of the Cγ3 coding region and 5' of the M315 VH coding region enabled the M315 scFv to be combined with the three different hinge-CH3 genes by PCR SOEing (FIG. 11). The products of this reaction were then digested with HindIII and SalI and subcloned into a pUC19 vector (FIG. 12). Two BamHI restriction enzyme sites inside the V regions of M315 were removed by QuickChange PCR (FIG. 13) using primers: BamHI VL1: at gcc aac tgg ata caa gaa aaa cc; BamHI VL2: gg ttt ttc ttg tat cca gtt ggc at, BamHI VH1: tgg aac tgg ata cgg cag ttt cc and BamHI VH2: gg aaa ctg ccg tat cca gtt cca. A following QuickChange PCR using primers: 3'VL stop1: gtc act gtc cta tga ggcctgcagggcc ggatcc gtcgactctag and 3'VL stop2: cta gag tcg ac ggatccggccctgcaggcc tca tag gac agt gac, were then performed to introduce a stop codon (bold), a SfiI and a BamHI restriction enzyme site (underlined) downstream of the coding region (FIG. 14).

The final construct is then digested with HindIII and BamHI and subcloned into the expression vector pLNOH$_2$ (FIG. 15) (Norderhaug, Olafsen et al. 1997).

The V region genes providing specificity for MHC class II had previously been cloned from the 14-4-4S hybridoma (Lunde, Western et al. 2002), which produces an Ab specific for the Ea chain (determinant Ia.7) of the I-E MHC class II molecule (Ozato, Mayer et al. 1980). Specific primers annealing to the exact ends of the V region sequences with tags designed to include restriction enzyme sites (underlined) or linker sequences (bold) with the complementay sequences (italic). The primer sequences were: 5'VL: gac att caattgaca cag tct tct cct gct tcc; 3'VL: gcc aga gcc acc tcc gcc aga tcc gcc tcc acc ttt gat ttc cag ctt ggt gcc; 5'VH: ggc gga ggt ggc tct ggc ggt ggc gga tcg cag gtc cag ctg cag cag t; 3'VH: ga cgtacg actcacc tga gga gac ggt gac tga gg. The V region genes giving specificity for the hapten NIP (Neuberger 1983) were designed with the similar tag sequences except for the 5'VL primer: 5'VL: ggtg tgcattcc cag gct gtt gtg act cag gaa; 3'VL: gcc aga gcc acc tcc gcc aga tcc gcc tcc acc tag gac agt cag ttt ggt acc t; 5'VH: ggc gga ggt ggc tct ggc ggt ggc gga tcg cag gtc caa ctg cag cag cc; 3'VH: ga cgtacg a ctc acc tga gga gac tgt gag agt ggt. The VL and VH were then joined by PCR SOEing (FIG. 16) and subcloned into the V cassette pLNOH$_2$ vector containing the hinge-CH3-scFvM315 genes (FIG. 17 and FIG. 18). Likewise, other V genes conferring a desired specificity are isolated from hybridomas or from phage selected from phage display libraries. They are then PCR amplified using primers designed in the same manner as above and subcloned after PCR SOEing in the targeting-cassette (FIGS. 17 and 18). Rearranged V$_H$ and VK genes conferring specificity for HLA-DP were PCR amplified from cDNA from the 22C1 hybridoma, which produces an antibody with pan HLA-DP specificity. The V genes were reamplified with new primers containing sites for direct cloning into the expression vectors pLNOK and pLNOH$_2$ (Norderhaug and Olafsen, 1997); 5'-VL, ggtgtgcattccgacattgtgctcacc; 3'-VL, cgtacgttctactcacgttttatttccagct; 5'-VH, gtgcattccgaggtgcagctgcaggagtct; 3'-VH, cgtacgactcacctgaggagaccgtagc. Furthermore, scFV was generated by PCR SOEing using the following primers:

5'VL,
g gtg tgcattc cga cat tgt gct cac c

3'VL:
gcc aga gcc acc tcc gcc aga tcc gcc tcc acc gtt tta ttt cca gct

5'VH:
ggc gga ggt ggc tct ggc ggt ggc gga tcg gag gtg cag ctg cag gag tct

3'VH,
cgtacg act cac ctg agg aga ccg tag c

In 3'VL and 5'VH the sequences in bold+italics are complementary and antiparallell, thus hybridising to generate the gene fragment encoding the linker region. Anti CD14 V regions are cloned from the mouse hybridoma 3C10 (ATCC).

The chemokine genes were cloned from thioglycolate stimulated peritoneal macrophages. 4 ml 2% thioglycolate were injected i.p. into Balb/c mice. 3 days later peritoneal macrophages were collected and mRNA was extracted with oligo (dT)-coated magnetic Dynabeads. First strand cDNA was made and used as template for PCR amplification of chemokine genes (RANTES and MIP-1α) using specific primers: 5'MIP-1α: ggtg tgcattc cgc gcc ata tgg agc tga cac, 3'MIP-1α: ga cgtacg act cac ctg cat tca gtt cca ggt cag tg 5'RANTES: ggtg tgcattc c gcc tca cca tat ggc tcg g 3'RANTES: ga cgtacg a ctc acc tga cat ctc caa ata gtt gat gta ttc. The different targeting unit genes were then digested with MunI and BsiWI or BsmI and BsiWI, respectively and sub-cloned into the V cassette pLNOH$_2$ vector containing the hinge-CH3-scFvM315 genes (FIG. 17 and FIG. 18). CD40 ligand is cloned from T cells that are activated with LPS for 4 hours before mRNA is extracted for preparation of cDNA. The cDNA is used as template in a PCR reaction with primers specific for the CD40 ligand sequence. Furthermore, this sequence is reamplified with primers designed to facilitate subcloning in the targeting cassette as described above.

Production and Purification of Vaccibodies

The pLNOH$_2$ vector carrying the Vaccibody genes was transfected into NSO cells by electroporation, and supernatants from single colonies resistant to 800 μg/ml G418 were analyzed for Vaccibody secretion after 2-3 weeks, using ELISA. DNP-BSA was used as coat, and biotinylated rat-anti mouse Vλ1/2 (9A8-bio) was used for detection. The NIP-specific Vaccibodies were additionally screened in an ELISA using NIP-BSA as coat. The cells selected for high Vaccibody production were grown in Rollerbottles (VWR) and affinity purified from supernatant using a column made by DNP-lysine (Sigma) coupled to fast flow Sepharose. The Vaccibodies were eluted with 0.05M DNP-glycine (Sigma) and the flow-through was run on an ion-exchange Cl-Dowex 1×8 resin column (Sigma). The eluted Vaccibodies were dialyzed against PBS/0.05% NaN3 and sterile PBS, before the vaccibody concentration were calculated from absorbance values at 280 nm.

Ab and Flow Cytometry

Ab and reagents used for flow cytometry were 9A8 biotin, FGK.45 biotin, streptavidin PerCP, anti-CD19 PE and anti-mIgG2a PE (BD Pharmingen). BALB/c spleen cells were double stained with anti-CD19 PE and Vaccibodies. Bound Vaccibodies were detected by 9A8-bio and streptavidin PerCP. Twenty thousand cells were run on FACSCalibur (BD Biosciences, Mountain View, Calif.) and analyzed using the WinMDI software.

Metabolic Labelling and Immunoprecipitation $2 \times 10^6$ cells were labelled for 6 h at 37° C. in RPMI lacking methionine, cysteine (BioWhittaker) containing 100 μCi $^{35}$-[S]-methionine, cysteine (Amersham). The SN was harvested and immunoprecipitated with rat anti-mouse Vλ1/2 (9A8) on a wheel ON at 4° C. 10 μl Dynabeads coated with sheep anti-rat IgG (Dynal AS, Oslo, Norway) were incubated with the precipitate for 1 h on a wheel and the Dynabeads were collected with a Dynal Magnetic Particle Concentrator rack (Dynal MPC). The beads were washed three times in ice cold PBS with 1% NP40 and resuspended in 10 μl 1× sample buffer. The proteins were eluted from the beads by incubating the samples at 95° C. for 3 minutes. The Vaccibodies were run on a 10% SDS-PAGE gel, with a 5% stacking gel, at 40 mA for 1 h, using a BIO RAD miniprotean II gel electrophoresis apparatus. The gels were subsequently fixed in 30% methanol and 10% acetic acid for 30 minutes prior to 30 min incubation with Amplify (Amersham), before drying and exposing to BIOMAX-MR film (Eastman Kodak Company, Utah, USA).

T Cell Proliferation Assay

Irradiated (2000 rad) BALB/c splenocytes ($5 \times 10^5$ cells/well) were used as a source of APC. Titrated amounts of different MHC CLASS II- and NIP-specific Vaccibodies were added to the splenocytes. A 91-107 λ2$^{315}$ synthetic peptide were used as a positive control. The assays were put up in 150 μl cultures in 96-well flat-bottom microtiter wells and incubated for 4 h at 37° C. (Lunde, Western et al. 2002). The cultures were then washed three times before addition of 200 μl polarized λ2$^{315}$-specific Th2 cells ($2 \times 10^4$) derived from TCR transgenic SCID mice. After 48 h, the cultures were pulsed for 16-24 h with 1 μCi $^3$[H] dThd. The cultures were harvested and, and incorporated $^3$[H] dThd was measured using a TopCount NXT scintillation counter (Packard, Meriden, Conn.).

In Vivo Experiments

BALB/c mice were injected subcutaneously (s.c.) with 200 μg or 20 μg purified Vaccibody proteins in PBS on day 0, 14 and 28. Blood samples were taken on day 14 and 28 before revaccination and then on day 35, 42 and 49, before they were sacrificed according to the Humane End Point procedure.

Measurement of Antibody Responses

Anti-idiotypic Abs against M315 were measured by ELISA. The wells were coated with 2 μg/ml M315. Anti-Id Ab in the sera were detected by a biotinylated anti-mouse Vκ Ab (187.1 bio), anti-mouse IgG1 bio or anti-mouse IgG2a bio (both from BD Pharmingen). Ab2.1-4 (an anti-Id mAb that bind λ2$^{315}$) was used as standard.

Vaccination

Protein vaccination: BALB/c mice were injected subcutaneously (s.c.) in the right flank region with 20 pg or 200 μg purified class II- or NIP specific Vaccibodies ($F_v^{I-E}$ $F_v^{315}$, $FV_v^{NIP}$ $F_v^{315}$) in PBS on day 0 and 14. PBS was injected as negative control. Blood samples were collected from the leg vein on different time points after the last immunization. Anti-idiotypic antibodies with specificity with specificity for $F_v^{315}$ were measured by ELISA. The wells were coated with 2 μg/ml M315. Anti-Id Ab in the sera were detected by a biotinylated anti-mouse κ mAb (187.1 bio). Ab2.1-4 (an anti-Id mAb binding $F_v^{315}$ (Kristoffersen, Hannestad et al. 1987) was used as standard.

Dna Vaccination and Electroporation

Five to ten weeks old Balb/c mice were purchased from Bomholtgaard (Ry, Denmark). The animals were anaesthetized by intraperitonal injection with 9 g Pentobarbital/mice and the legs were shaved. Conductive gel was applied at the skin and 50 μl vector DNA diluted in 0.9% NaCl, was injected into the quadriceps. Following injection, electroporation was performed, by applying rod electrodes to the skin near the site of the injection and subjecting the site to an electrical potential comprising 10 trains of 1000 pulses each, with a pulse length at two times 200 Sec (positive 200 Sec and negative 200 Sec) with 600 s interval between each pulse and with a current limit of 50 mA (about 150-174 V/cm) (Tollefsen, Tjelle et al. 2002).

Blood samples were collected from the leg vein on different time points and heart puncture was performed on the day they were sacrificed. Serum samples were analyzed for the presence of correctly folded Vaccibodies. The ELISA was performed with DNP-BSA as coat and 9A8-bio as detected Ab, as described above. In addition, serum samples were analyzed for anti-Id Abs by ELISA as described above.

Tumor Challenge

Protein Vaccibodies-MOPC315.4: BALB/c mice (6-10 weeks old) were injected s.c. with 160 μg class II- or NIP-specific Vaccibodies in PBS in the right flank region on day 0 and 14. On day 28, 1.6×10⁵ MOPC315.4 cells were injected s.c. on the right flank. Mice were inspected twice weekly. Tumor size development was monitored by palpation and use of a caliper. A tumor of 3 mm in diameter was scored as tumor take. Mice were killed when tumor size reached 20 mm with no sign of tumor necrosis.

DNA Vaccibodies-MOPC315.4: DNA vaccination was performed at day 0 as described above. On day 14, 1.6×10⁵ MOPC315.4 cells were injected s.c. in the right flank region. Tumor size development was monitored by palpation and use of a caliper. The mice were sacrificed when the tumor size reached 20 mm. Blood samples were collected on different time points from the leg vein. Levels of M315 myeloma protein in sera were quantified in a sandwich ELISA with Ab2.1-4 as coat by biotinylated anti-Cα (8D2) mAb as detection Ab. Tumor size, tumor take, survival curves and statistical analyses were calculated by use of Graph Pad Prism 3.0 software (San Diego, Calif.).

EXAMPLES

By way of example the following experiments demonstrate that Vaccibodies bind APC and are able to trigger both T cell and B cell immune response. Moreover, the following experiments show that Vaccibodies induce a strong immune response rendering adjuvants redundant. The experiments demonstrate that said molecule is capable of inducing an immune response against multiple myeloma and, further, the feasibility of treatment of mammals by immunization by means of Vaccibody DNA or Vaccibody protein. The experiments also demonstrate that another attractive approach is to target the Vaccibodies to surface molecules expressed exclusively on subsets of dendritic cells (DC), like e.g. chemokine receptors. The following examples are meant to illustrate how to make and use the invention. They are not intended to limit the scope of the invention in any manner or to any degree.

Example 1

Vaccibodies are produced and secreted as functional dimerized molecules and is itself bound by the anti-Vλ1/2 antibody (9A8) (Bogen 1989) and the anti-idiotypic antibody Ab2.1-4 (Lauritzsen, Weiss et al. 1994).

The M315 mAb binds the hapten di-nitro-phenyl (DNP) (Eisen, Simms et al. 1968). Therefore, to verify that Vaccibodies were produced, secreted and correctly folded as functional molecules, the antigenic units of Vaccibodies were tested in ELISA for their capability to bind DNP, 9A8 and Ab2.1-4 mAbs. FIG. 20$b$ shows that both the NIP-specific and the MHCII-specific Vaccibodies, that both have scFv³¹⁵, bind DNP, 9A8 and Ab2.1-4. This was the case with all Vaccibodies containing scFv³¹⁵, both the ones with long human dimerization unit, short human dimerization unit and murine dimerization unit (FIG. 5). We next tested the targeting units of the Vaccibodies. These were found to be correct; first, the NIP-specific Vaccibodies bound NIP-BSA in ELISA (FIG. 4 and FIG. 20$c$), while the MHCII-specific Vaccibodies did not (FIG. 20$c$). Second, the MHCII-specific Vaccibodies bound to I-E expressing BALB/c splenic B cells (H-2$^d$) as detected by flow cytometry, whereas the NIP-specific Vaccibodies did not (FIG. 3). To check for correct homodimerization, the Vaccibodies were metabolically labelled by growth of transfected cells in medium containing ³⁵S-methionine, vaccibodies were immunoprecipitated from supernatant using specific antibodies, and analyzed by SDS-PAGE. As would be expected from the theoretical consideration of FIG. 2, both the $F_v^{NIP}F_v^{315}$ and $F_v^{vI-E}F_v^{315}$ transfectomas secreted dimeric Vaccibodies of ~130 kDa. After reduction of disulfide bonds, the Vaccibodies are degraded to monomeric chains of ~65 kDa (FIG. 20$a$).

Example 2

MHC class II-specific Vaccibodies enhance λ2³¹⁵-specific stimulation of CD4+ T cells.

Class II-specific and non-targeting NIP-specific Vaccibodies were mixed with antigen presenting cells (APC) and compared for their ability to induce specific T cell activation. Irradiated BALB/c splenocytes were used as APC. The BALB/c strain has the H-2$^d$ haplotype, hence they express I-E$^d$ molecules necessary for both targeting of the MHC II-specific Vaccibodies and presentation of the λ2³¹⁵ epitope to specific CD4+ T cells.

The APC were pulsed with the different Vaccibodies for 4 h and subsequently washed. Washing was performed to reduce the chance that I-E$^d$-specific Vaccibodies in the culture medium could diminish T cell stimulation by blocking I-E$^d$ molecules (Lunde, Western et al. 2002). Polarized Th2 cells from mice transgenic for a λ2³¹⁵-specific I-E$^d$ restricted TCR (Lauritzsen, Weiss et al. 1993) were added as responder T cells. The dose response curve in FIG. 6 shows that the λ2³¹⁵ epitope was presented 100-1000 times more efficiently to TCR-transgenic Th2 cells when they were carried in the APC-targeted MHC II-specific Vaccibodies (both the ones with short and long human dimerization units) compared to the non-targeted NIP-specific Vaccibodies. It should be noted that Vaccibodies do not include an FcγR binding site; hence the NIP-specific Vaccibodies should not be able to enter cells via receptor-mediated endocytosis.

Example 3

Level of Anti-Idiotypic Antibodies in Sera of Mice that Received Vaccibodies as Proteins in Saline S.C. in the Absence of Adjuvant In the protein vaccination protocol, BALB/c mice were immunized twice, spaced two weeks apart, with 20 or 200 µg MHC II-specific Vaccibodies or NIP-specific Vaccibodies in PBS. Note that no adjuvant was employed. Sera from immunized mice taken at various time points after the second vaccination were then analyzed for anti-idiotypic antibodies binding M315 in ELISA. The MHC II-specific Vaccibodies elicited significant higher anti-idiotypic antibody responses after 14 days after the second immunization than did NIP-specific Vaccibodies. Vaccibodies with a long human dimerization unit induced best anti-idiotypic Ab responses (FIG. 7). Thus targeting of Vaccibodies enhanced anti-Id immuneresponses, however, by this route of immunization, also the non-targeted Vaccibodies induced some responses.

Example 4

Protein Vaccibodies Detected in Serum after Injection of DNA Intramuscularly and In Vivo Electroporation It has recently been described that skeletal muscle can produce antibodies after injection of Ig genes and electroporation (Tjelle 2004). We therefore investigated if functional Vaccibodies were produced by i.m. plasmid injection and electroporation. Since the $F_v^{I-E}F_v^{315}$ Vaccibodies are specific for I-E$^d$ molecules present in BALB/c (H-2d), these Vaccibodies should be rapidly absorbed by the I-E$^d$ positive cells in BALB/c. By contrast, the non-targeted FvNIP $F_v^{315}$ Vaccibodies should not be absorbed. Indeed, 14 days after a single injection of 50 μg Vaccibody plasmid in quadriceps and electroporation, $F_v^{NIP} F_v^{315}$ Vaccibody protein was detected in significant amounts in serum, while there was no detectable $F_v^{I-E} F_v^{315}$ (FIG. 21a).

Example 5

Anti-Id Antibodies in Serum after Injection of Vaccibody DNA Intramuscularly and Electroporation Analysis of the same day 14 sera samples for anti-idiotypic antibodies demonstrated that mice i.m. injected/electroporated with the MHC class II-targetd $F_v^{I-E} F_v^{315}$ Vaccibody DNA, had developed antibodies that bound idiotypic Fv from the MOPC315.4 tumor (FIG. 21b). This result was in distinct contrast to the lack of any anti-idiotypic antibody response in mice injected with the non-targeted $F_v^{NIP} F_v^{315}$ Vaccibody DNA (FIG. 21b). Taken together with the results described in example 4, the results demonstrate a formidable effect of targeting to MHC class II (I-E$^d$) positive cells for development of a strong humoral response. Control mice injected i.m. with 0.9% NaCl followed by electroporation had neither Vaccibodies nor anti-idiotypic Abs in day 14 sera (FIG. 21a-c).

Example 6

Induction of Protective Immunity Against the MOPC315.4 Myeloma: Vaccibody DNA injection/electroporation Intramuscular vaccination with MHC class II-targeted $F_v^{I-E} F_v^{315}$ Vaccibody plasmids and subsequent electroporation induced strong protection against a challenge with MOPC315.4 myeloma cells, p<0.001, compared to control mice injected with 0.9% NaCl and electroporated (FIG. 23). By contrast, non-targeted $F_v^{NIP} F_v^{315}$ Vaccibody plasmid immunization was ineffective compared to the saline control group, p=0.2739 (FIG. 23). The appearance of tumor was delayed in mice vaccinated with $F_v^{I-E} F_v^{315}$ compared to $F_v^{NIP} F_v^{315}$ (FIG. 22). One of the $F_v^{I-E} F_v^{315}$ vaccinated mice developed a tumor of maximum 6 mm (day 20) in diameter that regressed and was completely undetectable from day 28 (data not shown). The presence of M315 myeloma protein in sera confirmed the tumor size measurements (FIG. 24). These results show that protection against the MOPC315.4 myeloma can be achieved by i.m. DNA vaccine followed by electroporation and that the protection requires targeting of the tumor-derived scFv to MHC class II (I-E$^d$) positive cells.

Example 7

Chemokines are Functional as Targeting Units in the Vaccibody Format

Supernatant from cells transfected with Vaccibody construct with MIP-1α in the targeting unit, long human dimerization unit and M315 scFv in the antigenic unit, were collected and tested in ELISA for binding to an anti-mouse MIP-1α mAb and 9A8 bio. The Vaccibodies containing MIP-1α bound to anti-MIP-1α mAb, while the NIP-specific Vaccibodies did not (FIG. 25).

Example 8

The Chemokine RANTES is Functional as Targeting Unit in the Vaccibody Format

In the same manner, a vector with a gene encoding Vaccibodies like those described in example 7 was produced, with the exception that the targeting unit was the mouse chemokine RANTES. Supernatant from cells transfected with this construct was collected and tested in ELISA for the presence of Vaccibodies. The experiment showed that this Vaccibody variant was expressed and exported as a functional molecule.

Example 9

Flaggelin as Targeting Unit in the Vaccibody Format

In the same manner, a vector with a gene encoding Vaccibodies like those described in example 7 was produced, with the exception that the targeting unit was flaggelin. Supernatant from cells transfected with this construct will be collected and tested in ELISA for the presence of Vaccibodies.

Example 10

Soluble CD40 Ligand as Targeting Unit in the Vaccibody Format

In the same manner, a vector with a gene encoding Vaccibodies like those described in example 7 was produced, with the exception that the targeting unit was soluble CD 40 ligand from the mouse. Supernatant from cells transfected with this construct will be collected and tested in ELISA for the presence of Vaccibodies.

Example 11

Anti-Toll-Like-Receptor 2 as Targeting Unit in the Vaccibody Format

In the same manner, a vector with a gene encoding Vaccibodies like those described in example 7 was produced, with the exception that the targeting unit was a scFv with specificity for toll-like-receptor 2 from the mouse. Supernatant from cells transfected with this construct will be collected and tested in ELISA for the presence of Vaccibodies.

Example 12

Anti-CD14 is Functional as Targeting Units in the Vaccibody Format

In the same manner, a vector with a gene encoding Vaccibodies like those described in example 7 was produced, with the exception that the targeting unit was scFv with specificity for human CD 14. Supernatant from cells transfected with this construct was collected and tested in ELISA for the presence of Vaccibodies. The results showed that this Vaccibody variant was expressed and exported as a functional molecule.

Example 13

Anti-HLA-DP is Functional as Targeting Units in the Vaccibody Format

In the same manner, a vector with a gene encoding Vaccibodies like those described in example 7 was produced, with the exception that the targeting unit was scFv with specificity for HLA-DP. Supernatant from cells transfected with this construct was collected and tested in ELISA for the presence of Vaccibodies. The results showed that this Vaccibody variant was expressed and exported as a functional molecule.

Example 14

Tuberculosis Antigen in the Vaccibody Antigenic Cassette

A nucleic acid encoding a tuberculosis antigen (cattle antigen) will be inserted into the antigenic unit of the Vaccibody construct.

Example 15

Telomerase Antigen in the Vaccibody Antigenic Cassette hTERT, an antigenic region of the telomerase ribonucleoprotein, will be inserted into the antigenic unit of the Vaccibody construct.

Example 16

HIV Gp120 Antigenic in the Vaccibody Antigenic Cassette

A nucleic acid encoding a gp120 derived molecule will be inserted into the antigenic unit of the Vaccibody construct.

Example 17

Vaccibodies with Patient Specific scFv of Myeloma Origin in the Antigenic Cassette This study has been initiated, but has not yet been completed.

Bone marrow aspirate from patients suffering from multiple myeloma can be collected. The mononuclear cells (MNC) can be separated using a density gradient solution of Ficoll-Isopaque (Lymphoprep™ from Axis-Shield PoC AS). Total RNA can be isolated (TRIzol® Reagent from Invitrogen™ Life Technologies) from MNC, and cDNA can be made from mRNA (First-Strand cDNA Synthesis Kit from Amersham Biosciences (Not I-d(T)18 bifunctional primer)). This cDNA can be used as template in PCR with primers that amplify the V genes of the heavy or light chain of the multiple myeloma Ig. The sense primers are family specific and localized in the leader regions (VH1-7, VK1-6 and VL1-10), and the anti-sense primers are localized in the first part of the C regions (one primer each for IgG, IgA, kappa and lambda). PCR products can be ligated into a vector (pGEM®-T Easy Vector from Promega), and transformed into *E. coli*. DNA samples isolated from individual colonies can be sequenced. Getting the same sequence from three different colonies originating from three different PCRs confirms that the V regions from the myeloma Ig have been isolated. PCR SOEing can be performed and reamplification is done with primers including tags with sites for SfiI as described in FIG. 19. For one patient such primers had the sequence:

```
5'TAVH
5'  ACGTAGGCCTCGGTGGCCTGCAGATCACCTTGAAGGAGTCT

3'TAVK
5' GATCCGGCCCTGCAGGCCTCATTTGATCTCCAGCTTGGTCCC
```

The resulting vector can be transiently transfected into 293E cells. Supernatants can be tested in ELISA for the presence of such Vaccibodies. They can also be injected into BALB/c mice. The presence of anti-Idiotypic antibodies can be measured in ELISAs against serum from the mice and serum from the patients.

All references cited herein are incorporated in their entireties by reference.

The description of the invention is merely exemplary in nature and, thus, variations that do not depart from the gist of the invention are intended to be within the scope of the invention. Such variations are not to be regarded as a departure from the spirit and scope of the invention.

REFERENCES

Bendandi, M., C. D. Gocke, et al. (1999). "Complete molecular remissions induced by patient-specific vaccination plus granulocyte-monocyte colony-stimulating factor against lymphoma." Nat Med 5(10): 1171-7.

Biragyn, A., P. A. Ruffini, et al. (2002). "Toll-like receptor 4-dependent activation of dendritic cells by beta-defensin 2." Science 298(5595): 1025-9.

Biragyn, A., K. Tani, et al. (1999). "Genetic fusion of chemokines to a self tumor antigen induces protective, T-cell dependent antitumor immunity." Nat Biotechnol 17(3): 253-8.

Bogen, B. (1989). "Monoclonal antibodies specific for variable and constant domains of murine lambda chains." Scand J Immunol 29(3): 273-9.

Bogen, B., Peripheral T cell tolerance as a tumor escape mechanism: deletion of CD4+ T cells specific for a monoclonal immunoglobulin idiotype secreted by a plasmacytoma. Eur J Immunol. 1996 November; 26(11):2671-9.

Bogen, B., L. Gleditsch, et al. (1992). "Weak positive selection of transgenic T cell receptor-bearing thymocytes: importance of major histocompatibility complex class II, T cell receptor and CD4 surface molecule densities." Eur J Immunol 22(3): 703-9.

Bogen, B. and J. D. Lambris (1989). "Minimum length of an idiotypic peptide and a model for its binding to a major histocompatibility complex class II molecule." Embo J 8(7): 1947-52.

Bogen, B., B. Malissen, et al. (1986). "Idiotope-specific T cell clones that recognize syngeneic immunoglobulin fragments in the context of class II molecules." Eur J Immunol 16(11): 1373-8.

Casten, L. A. and S. K. Pierce (1988). "Receptor-mediated B cell antigen processing. Increased antigenicity of a globular protein covalently coupled to antibodies specific for B cell surface structures." J Immunol 140(2): 404-10.

Eisen, H. N., E. S. Simms, et al. (1968). "Mouse myeloma proteins with antihapten antibody acitivity. The protein produced by plasma cell tumor MOPC-315." Biochemistry 7(11): 4126-34.

Hakim, I., S. Levy, et al. (1996). "A nine-amino acid peptide from IL-1 beta augments antitumor immune responses induced by protein and DNA vaccines." J Immunol 157 (12): 5503-11.

Hough, D. W., R. P. Eady, et al. (1976). "Anti-idiotype sera raised against surface immunoglobulin of human neoplastic lymphocytes." J Exp Med 144(4): 960-9.

Huang, H. I., P. Y. Wu, et al. (2004). "Improved immunogenicity of a self tumor antigen by covalent linkage to CD40 ligand." Int J Cancer 108(5): 696-703.

King, C. A., M. B. Spellerberg, et al. (1998). "DNA vaccines with single-chain Fv fused to fragment C of tetanus toxin induce protective immunity against lymphoma and myeloma." Nat Med 4(11): 1281-6.

Kristoffersen, G., K. Hannestad, et al. (1987). "Two M315 idiotypes defined by isologous monoclonal antibodies: one depends on germline and the other on mutated murine lambda 2 light chain sequences." Scand J Immunol 26(5): 535-46.

Lauritzsen, G. F., S. Weiss, et al. (1993). "Anti-tumour activity of idiotype-specific, MHC-restricted Th1 and Th2 clones in vitro and in vivo." Scand J Immunol 37(1): 77-85.

Lauritzsen, G. F., S. Weiss, et al. (1994). "Naive idiotype-specific CD4+ T cells and immunosurveillance of B-cell tumors." Proc Natl Acad Sci USA 91(12): 5700-4.

Lunde, E., L. A. Munthe, et al. (1999). "Antibodies engineered with IgD specificity efficiently deliver integrated T-cell epitopes for antigen presentation by B cells." Nat Biotechnol 17(7): 670-5.

Lunde, E., I. B. Rasmussen, et al. (2001). "'Troy-bodies': antibodies as vector proteins for T cell epitopes." Biomol Eng 18(3): 109-16.

Lunde, E., K. H. Western, et al. (2002). "Efficient delivery of T cell epitopes to APC by use of MHC class II-specific Troybodies." J Immunol 168(5): 2154-62.

Neuberger, M. S. (1983). "Expression and regulation of immunoglobulin heavy chain gene transfected into lymphoid cells." Embo J 2(8): 1373-8.

Norderhaug, L., T. Olafsen, et al. (1997). "Versatile vectors for transient and stable expression of recombinant antibody molecules in mammalian cells." J Immunol Methods 204(1): 77-87.

Olafsen, T., I. B. Rasmussen, et al. (1998). "IgM secretory tailpiece drives multimerisation of bivalent scFv fragments in eukaryotic cells." Immunotechnology 4(2): 141-53.

Ozato, K., N. Mayer, et al. (1980). "Hybridoma cell lines secreting monoclonal antibodies to mouse H-2 and Ia antigens." J Immunol 124(2): 533-40.

Ravetch, J. V. and S. Bolland (2001). "IgG Fc receptors." Annu Rev Immunol 19: 275-90.

Sirisinha, S. and H. N. Eisen (1971). "Autoimmune-like antibodies to the ligand-binding sites of myeloma proteins." Proc Natl Acad Sci USA 68(12): 3130-5.

Snider, D. P. and D. M. Segal (1987). "Targeted antigen presentation using crosslinked antibody heteroaggregates." J Immunol 139(5): 1609-16.

Tao, M. H. and R. Levy (1993). "Idiotype/granulocyte-macrophage colony-stimulating factor fusion protein as a vaccine for B-cell lymphoma." Nature 362(6422): 755-8.

Tjelle, T., Corthay, A., Lunde, E., Sandlie, I., Michaelsen, T E., Mathiesen, I and Bogen, B. (2004). "Monoclonal antibodies produced by muscle after plasmid injection and electroporation." J Mol. Ther.

Tollefsen, S., T. Tjelle, et al. (2002). "Improved cellular and humoral immune responses against *Mycobacterium tuberculosis* antigens after intramuscular DNA immunisation combined with muscle electroporation." Vaccine 20(27-28):3370-8.

What is claimed is:

1. A method for inducing an immune response against an antigen in an animal, including a human being, the method comprising administering to the animal, an effective amount of at least one nucleic acid which encodes a monomer unit of a dimeric recombinant antibody-based molecule, which comprises two such monomer units that are connected through a dimerization motif, wherein said dimerization motif
consists of a hinge region and a carboxyterminal C domain and comprises a hinge region and a Cγ3 domain of each monomer unit, wherein each hinge region contributes to dimerization via disulfide bridging to the other hinge region and each Cγ3 domain contributes to dimerization via hydrophobic interactions to the other Cγ3 domain,
and wherein said monomer units each comprises
an antigenic unit derived from said antigen, and
a targeting unit for an antigen presenting cell,
and wherein said monomer units both lack a CH2 domain, whereby administration of said nucleic acid induces production of said recombinant dimeric antibody-based molecule in said animal whereby an immune response is induced against said antigen.

2. The method of claim 1, wherein administering the nucleic acid comprises delivering the nucleic acid by electroporation.

3. The method of claim 1, wherein said targeting unit(s) is/are a single chain fragment variable of Ig (scFv).

4. The method of claim 3, wherein said scFv is anti-HLA, anti-CD14, anti-CD40, or anti-toll-like receptor.

5. The method of claim 4, wherein said anti-HLA is anti-HLA-DP.

6. The method of claim 4, wherein said anti-toll-like receptor is anti-toll-like receptor 2.

7. The method of claim 1, wherein at least one targeting unit is a ligand.

8. The method of claim 7, wherein said ligand is soluble CD40 ligand or a chemokine.

9. The method of claim 7, wherein said ligand is a chemokine.

10. The method of claim 9, wherein said chemokine is RANTES or MIP-1α.

11. The method of claim 9, wherein said chemokine is MIP-1α.

12. The method of claim 1, wherein at least one targeting unit is a bacterial antigen.

13. The method of claim 12, wherein the bacterial antigen is a flaggelin.

14. The method of claim 1, wherein the targeting units have the ability to target antigen presenting cells (APC).

15. The method of claim 1, wherein the targeting units have the ability to target HLA, CD14, CD40, toll-like receptors, or a chemokine receptors.

16. The method of claim 15, wherein said HLA is HLA-DP.

17. The method of claim 1, wherein the targeting units have the ability to target chemokine receptors.

18. The method of claim 1, wherein the antigenic unit(s) is/are an antigenic scFv.

19. The method of claim 18, wherein the antigenic scFv is derived from a monoclonal Ig produced by myeloma or lymphoma.

20. The method of claim 18, wherein the antigenic unit(s) is/are a telomerase, or a functional part thereof.

21. The method of claim 20, wherein said telomerase is hTERT.

22. The method of claim 1, wherein the antigenic unit(s) is/are derived from a bacterium.

23. The method of claim 22, wherein the bacterium derived antigenic unit(s) is/are a tuberculosis antigen.

24. The method of claim 1, wherein the antigenic unit(s) is/are derived from a virus.

25. The method of claim 24, wherein the virus derived antigenic unit(s) is/are derived from HIV.

26. The method of claim 25, wherein the HIV derived antigenic unit(s) is/are derived from gp120.

27. The method of claim 1, wherein the carboxyterminal C domain is derived from IgG.

28. The method of claim 1, wherein the dimerization motif has the ability to homodimerize.

29. The method of claim 1, comprising administering a vector comprising the nucleic acid.

* * * * *

SEQUENCE LISTING

```
<160> NUMBER OF SEQ ID NOS: 43

<210> SEQ ID NO 1
<211> LENGTH: 25
<212> TYPE: DNA
<213> ORGANISM: Artificial sequence
<220> FEATURE:
<223> OTHER INFORMATION: Synthetic primer 5'h4

<400> SEQUENCE: 1
tagcaagctt ggccagcgca gggag                                           25

<210> SEQ ID NO 2
<211> LENGTH: 33
<212> TYPE: DNA
<213> ORGANISM: Artificial sequence
<220> FEATURE:
<223> OTHER INFORMATION: Synthetic primer 3'CH3

<400> SEQUENCE: 2
caggccaccg aggcctttac ccggagacag gga                                  33

<210> SEQ ID NO 3
<211> LENGTH: 75
<212> TYPE: DNA
<213> ORGANISM: Artificial sequenc
<220> FEATURE:
<223> OTHER INFORMATION: Synthetic primer Qh1a

<400> SEQUENCE: 3
ctccaatctt ctctctgcag agctcaaaac cccacttggt gacacaactc acacagagcc     60
caaatcttgt gacac                                                      75

<210> SEQ ID NO 4
<211> LENGTH: 76
<212> TYPE: DNA
<213> ORGANISM: Artificial sequence
```

```
<220> FEATURE:
<223> OTHER INFORMATION: Synthetic primer Qh1b

<400> SEQUENCE: 4
gtgtcacaag atttgggctc tgtgtgagtt gtgtcaccaa gtggggtttt gagctctgca    60
gagagaagat tgggag                                                    76

<210> SEQ ID NO 5
<211> LENGTH: 27
<212> TYPE: DNA
<213> ORGANISM: Artificial sequence
<220> FEATURE:
<223> OTHER INFORMATION: Synthetic primer 5' hinge

<400> SEQUENCE: 5
tagcaagctt cagagcccag cgggccc                                        27

<210> SEQ ID NO 6
<211> LENGTH: 46
<212> TYPE: DNA
<213> ORGANISM: Artificial sequence
<220> FEATURE:
<223> OTHER INFORMATION: Synthetic primer 3' hinge

<400> SEQUENCE: 6
tccacctccg ctgcttccac cgcctgggca tttgtgacac tccttg                   46

<210> SEQ ID NO 7
<211> LENGTH: 44
<212> TYPE: DNA
<213> ORGANISM: Artificial sequence
<220> FEATURE:
<223> OTHER INFORMATION: Synthetic primer 5'CH3

<400> SEQUENCE: 7
ggaagcagcg gaggtggaag tggagggcta gtcagagctc caca                     44

<210> SEQ ID NO 8
<211> LENGTH: 34
<212> TYPE: DNA
<213> ORGANISM: Artificial sequence
<220> FEATURE:
<223> OTHER INFORMATION: Synthetic primer 3'CH3

<400> SEQUENCE: 8
caggccaccg aggccacccg agaccggga gatg                                 34

<210> SEQ ID NO 9
<211> LENGTH: 36
<212> TYPE: DNA
<213> ORGANISM: Artificial sequence
<220> FEATURE:
<223> OTHER INFORMATION: Synthetic primer 5'vh

<400> SEQUENCE: 9
ggcctcggtg gcctggatgt acagcttcag gagtca                              36

<210> SEQ ID NO 10
<211> LENGTH: 54
<212> TYPE: DNA
<213> ORGANISM: Artificial sequence
<220> FEATURE:
<223> OTHER INFORMATION: Synthetic primer 3'Vh
```

```
<400> SEQUENCE: 10
gccagagcca cctccgccag atccgcctcc acctgaggag actgtgagag tggt         54

<210> SEQ ID NO 11
<211> LENGTH: 51
<212> TYPE: DNA
<213> ORGANISM: Artificial sequence
<220> FEATURE:
<223> OTHER INFORMATION: Synthetic primer 5'vl

<400> SEQUENCE: 11
ggcggaggtg gctctggcgg tggcggatct caggctgttg tgactcagga a            51

<210> SEQ ID NO 12
<211> LENGTH: 30
<212> TYPE: DNA
<213> ORGANISM: Artificial sequence
<220> FEATURE:
<223> OTHER INFORMATION: Synthetic primer 3'vl

<400> SEQUENCE: 12
gacgtcgact aggacagtga ccttggttcc                                    30

<210> SEQ ID NO 13
<211> LENGTH: 25
<212> TYPE: DNA
<213> ORGANISM: Artificial sequence
<220> FEATURE:
<223> OTHER INFORMATION: Synthetic primer BamH1 VL1

<400> SEQUENCE: 13
atcccaactg gatacaagaa aaacc                                         25

<210> SEQ ID NO 14
<211> LENGTH: 25
<212> TYPE: DNA
<213> ORGANISM: Artificial sequence
<220> FEATURE:
<223> OTHER INFORMATION: Synthetic primer BamH1 VL2

<400> SEQUENCE: 14 ggttttttctt gtatccagtt ggcat                                        25

<210> SEQ ID NO 15
<211> LENGTH: 23
<212> TYPE: DNA
<213> ORGANISM: Artificial sequence
<220> FEATURE:
<223> OTHER INFORMATION: Synthetic primer BamH1 VH1

<400> SEQUENCE: 15
tggaactgga tacggcagtt tcc                                           23

<210> SEQ ID NO 16
<211> LENGTH: 23
<212> TYPE: DNA
<213> ORGANISM: Artificial sequence
<220> FEATURE:
<223> OTHER INFORMATION: Synthetic primer BamH1 VH2

<400> SEQUENCE: 16
ggaaactgcc gtatccagtt cca                                           23
```

-continued

```
<210> SEQ ID NO 17
<211> LENGTH: 45
<212> TYPE: DNA
<213> ORGANISM: Artificial sequence
<220> FEATURE:
<223> OTHER INFORMATION: Synthetic primer 3'VL stop1

<400> SEQUENCE: 17
gtcactgtcc tagtaggcct gcagggccgg atccgtcgac tctag          45

<210> SEQ ID NO 18
<211> LENGTH: 45
<212> TYPE: DNA
<213> ORGANISM: Artificial sequence
<220> FEATURE:
<223> OTHER INFORMATION: Synthetic primer 3'VL stop 2

<400> SEQUENCE: 18
ctagagtcga cggatccggc cctgcaggcc tcataggaca gtgac          45

<210> SEQ ID NO 19
<211> LENGTH: 33
<212> TYPE: DNA
<213> ORGANISM: Artificial sequence
<220> FEATURE:
<223> OTHER INFORMATION: Synthetic primer 5'vl

<400> SEQUENCE: 19
gacattcaat tgacacagtc ttctcctgct tcc                       33

<210> SEQ ID NO 20
<211> LENGTH: 54
<212> TYPE: DNA
<213> ORGANISM: Artificial sequence
<220> FEATURE:
<223> OTHER INFORMATION: Synthetic primer 3'VL

<400> SEQUENCE: 20
gccagagcca cctccgccag atccgcctcc acctttgatt tccagcttgg tgcc   54

<210> SEQ ID NO 21
<211> LENGTH: 48
<212> TYPE: DNA
<213> ORGANISM: Artificial sequence
<220> FEATURE:
<223> OTHER INFORMATION: Synthetic primer 5'vh

<400> SEQUENCE: 21
ggcggaggtg gctctggcgg tggcggatcg caggtccagc tgcagcag        48

<210> SEQ ID NO 22
<211> LENGTH: 35
<212> TYPE: DNA
<213> ORGANISM: Artificial sequence
<220> FEATURE:
<223> OTHER INFORMATION: Synthetic primer 3'vh

<400> SEQUENCE: 22
gacgtactac tcacctgagg agacggtgac tgagg                     35

<210> SEQ ID NO 23
<211> LENGTH: 33
<212> TYPE: DNA
<213> ORGANISM: Artificial sequence
<220> FEATURE:
<223> OTHER INFORMATION: Synthetic primer 5'vl 2nd
```

<400> SEQUENCE: 23
ggtgtgcatt cccaggctgt tgtgactcag gaa                            33

<210> SEQ ID NO 24
<211> LENGTH: 55
<212> TYPE: DNA
<213> ORGANISM: Artificial sequence
<220> FEATURE:
<223> OTHER INFORMATION: Synthetic primer 3'vl 2nd

<400> SEQUENCE: 24
gccagagcca cctccgccag atccgcctcc acctaggaca gtcagtttgg tacct     55

<210> SEQ ID NO 25
<211> LENGTH: 50
<212> TYPE: DNA
<213> ORGANISM: Artificial sequence
<220> FEATURE:
<223> OTHER INFORMATION: Synthetic primer 5'vh 2nd

<400> SEQUENCE: 25
ggcggaggtg gctctggcgg tggcggatcg caggtccaac tgcagcagcc           50

<210> SEQ ID NO 26
<211> LENGTH: 36
<212> TYPE: DNA
<213> ORGANISM: Artificial sequence
<220> FEATURE:
<223> OTHER INFORMATION: Synthetic primer 3'vh 2nd

<400> SEQUENCE: 26
gacgtacgac tcacctgagg agactgtgag agtggt                         36

<210> SEQ ID NO 27
<211> LENGTH: 27
<212> TYPE: DNA
<213> ORGANISM: Artificial sequence
<220> FEATURE:
<223> OTHER INFORMATION: Synthetic primer 5'vl 3rd

<400> SEQUENCE: 27
ggtgtgcatt ccgacattgt gctcacc                                   27

<210> SEQ ID NO 28
<211> LENGTH: 31
<212> TYPE: DNA
<213> ORGANISM: Artificial sequence
<220> FEATURE:
<223> OTHER INFORMATION: Synthetic primer 3'vl 3rd

<400> SEQUENCE: 28
cgtacgttct actcacgttt tatttccagc t                              31

<210> SEQ ID NO 29
<211> LENGTH: 30
<212> TYPE: DNA
<213> ORGANISM: Artificial sequence
<220> FEATURE:
<223> OTHER INFORMATION: Synthetic primer 5'vh 3rd

<400> SEQUENCE: 29
gtgcattccg aggtgcagct gcaggagtct                                30

<210> SEQ ID NO 30
<211> LENGTH: 28
<212> TYPE: DNA
<213> ORGANISM: Artificial sequence
<220> FEATURE:
<223> OTHER INFORMATION: Synthetic primer 3'vh 3rd

<400> SEQUENCE: 30
cgtacgactc acctgaggag accgtagc       28

<210> SEQ ID NO 31
<211> LENGTH: 27
<212> TYPE: DNA
<213> ORGANISM: Artificial sequence
<220> FEATURE:
<223> OTHER INFORMATION: Synthetic primer 5'vl 4th

<400> SEQUENCE: 31
ggtgtgcatt ccgacattgt gctcacc       27

<210> SEQ ID NO 32
<211> LENGTH: 48
<212> TYPE: DNA
<213> ORGANISM: Artificial sequence
<220> FEATURE:
<223> OTHER INFORMATION: Synthetic primer 3'vl 4th

<400> SEQUENCE: 32
gccagagcca cctccgccag atccgcctcc accgttttat ttccagct       48

<210> SEQ ID NO 33
<211> LENGTH: 51
<212> TYPE: DNA
<213> ORGANISM: Artificial sequence
<220> FEATURE:
<223> OTHER INFORMATION: Synthetic primer 5'vh 4th

<400> SEQUENCE: 33
ggcggaggtg gctctggcgg tggcggatcg gaggtgcagc tgcaggagtc t       51

<210> SEQ ID NO 34
<211> LENGTH: 29
<212> TYPE: DNA
<213> ORGANISM: Artificial sequence
<220> FEATURE:
<223> OTHER INFORMATION: Synthetic primer 3'vh 4th

<400> SEQUENCE: 34
cgttacgact cacctgagga gaccgtagc       29

<210> SEQ ID NO 35
<211> LENGTH: 32
<212> TYPE: DNA
<213> ORGANISM: Artificial sequence
<220> FEATURE:
<223> OTHER INFORMATION: Synthetic primer 5'MIP-1a

<400> SEQUENCE: 35
ggtgtgcatt ccgcgccata tggagctgac ac       32

<210> SEQ ID NO 36
<211> LENGTH: 37
<212> TYPE: DNA
<213> ORGANISM: Artificial sequence
<220> FEATURE:
<223> OTHER INFORMATION: Synthetic primer 3'MIP-1a

<400> SEQUENCE: 36
gacgtacgac tcacctgcat tcagttccag gtcagtg                              37

<210> SEQ ID NO 37
<211> LENGTH: 31
<212> TYPE: DNA
<213> ORGANISM: Artificial sequence
<220> FEATURE:
<223> OTHER INFORMATION: Synthetic primer 5' rantes

<400> SEQUENCE: 37
ggtgtgcatt ccgcctcacc atatggctcg g                                    31

<210> SEQ ID NO 38
<211> LENGTH: 42
<212> TYPE: DNA
<213> ORGANISM: Artificial sequence
<220> FEATURE:
<223> OTHER INFORMATION: Synthetic primer 3' rantes

<400> SEQUENCE: 38
gacgtacgac tcacctgaca tctccaaata gttgatgtat tc                        42

<210> SEQ ID NO 39
<211> LENGTH: 41
<212> TYPE: DNA
<213> ORGANISM: Artificial sequence
<220> FEATURE:
<223> OTHER INFORMATION: Synthetic primer 5'tavh

<400> SEQUENCE: 39
acgtaggcct cggtggcctg cagatcacct tgaaggagtc t                         41

<210> SEQ ID NO 40
<211> LENGTH: 42
<212> TYPE: DNA
<213> ORGANISM: Artificial sequence
<220> FEATURE:
<223> OTHER INFORMATION: Synthetic primer 5'tavk

<400> SEQUENCE: 40
gatccggccc tgcaggcctc atttgatctc cagcttggtc cc                        42

<210> SEQ ID NO 41
<211> LENGTH: 5
<212> TYPE: PRT
<213> ORGANISM: Artificial sequence
<220> FEATURE:
<223> OTHER INFORMATION: Peptide linker

<400> SEQUENCE: 41

Gly Leu Ser Gly Leu
1               5

<210> SEQ ID NO 42
<211> LENGTH: 15
<212> TYPE: PRT
<213> ORGANISM: Artificial sequence
<220> FEATURE:
<223> OTHER INFORMATION: Peptide linker Fig 8&9

<400> SEQUENCE: 42

Gly Gly Gly Ser Ser Gly Gly Gly Ser Ser Gly Gly Gly Ser Ser
1               5                   10                  15

-continued

```
<210> SEQ ID NO 43
<211> LENGTH: 15
<212> TYPE: PRT
<213> ORGANISM: Artificial sequence
<220> FEATURE:
<223> OTHER INFORMATION: Peptide linker Fig 10&11

<400> SEQUENCE: 43

Gly Gly Gly Gly Ser Gly Gly Gly Gly Ser Gly Gly Gly Gly Ser
1               5                   10                  15
```